(12) United States Patent
Martini et al.

(10) Patent No.: US 9,307,938 B2
(45) Date of Patent: *Apr. 12, 2016

(54) CONTROLLING TRANSFER OF OBJECTS AFFECTING OPTICAL CHARACTERISTICS

(71) Applicant: Palo Alto Research Center Incorporated, Palo Alto, CA (US)

(72) Inventors: Joerg Martini, San Francisco, CA (US); Jeffrey Roe, San Ramon, CA (US); Peter Kiesel, Palo Alto, CA (US); Michael Bassler, Mainz (DE); Alan Bell, Mountain View, CA (US); Richard H. Bruce, Soquel, CA (US); Noble M. Johnson, Menlo Park, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,236

(22) Filed: Nov. 27, 2012

(65) Prior Publication Data
US 2013/0085352 A1    Apr. 4, 2013

Related U.S. Application Data

(63) Continuation of application No. 11/957,610, filed on Dec. 17, 2007, now Pat. No. 8,320,983.

(51) Int. Cl.
*A61B 5/1455* (2006.01)
*A61B 5/1459* (2006.01)
(Continued)

(52) U.S. Cl.
CPC ........... *A61B 5/1459* (2013.01); *A61B 5/14532* (2013.01); *G01N 21/03* (2013.01); *G01N 21/8507* (2013.01); *G01N 21/39* (2013.01)

(58) Field of Classification Search
CPC ............. A61B 5/14532; A61B 5/1455; A61B 5/14551; A61B 5/0059; G01N 33/48; G01N 21/1702; G01N 21/8507; G01N 21/253; G01N 21/29; G01N 21/534

USPC ......... 600/310, 316, 317, 322, 329, 341, 342, 600/473, 476; 435/14, 25, 287.9; 422/82.08, 82.09; 356/39, 450, 454, 356/433, 436, 440–442

See application file for complete search history.

(56) References Cited

U.S. PATENT DOCUMENTS

| 2,708,389 | A | 5/1955 | Kavanagh |
| 3,915,573 | A | 10/1975 | Knoll et al. |

(Continued)

FOREIGN PATENT DOCUMENTS

| DE | 19540456 | 5/1997 |
| DE | 10030920 | 1/2002 |

(Continued)

OTHER PUBLICATIONS

File History for U.S. Appl. No. 11/957,610, 264 pages.

(Continued)

*Primary Examiner* — Tse Chen
*Assistant Examiner* — Chu Chuan (JJ) Liu
(74) *Attorney, Agent, or Firm* — Hollingsworth Davis, LLC

(57) ABSTRACT

An implantable product such as an article, device, or system can include analyte and non-analyte containers in parts that can be operated as optical cavities. The product can also include fluidic components such as filter assemblies that control transfer of objects that affect or shift spectrum features or characteristics such as by shifting transmission mode peaks or reflection mode valleys, shifting phase, reducing maxima or contrast, or increasing intermediate intensity width such as full width half maximum (FWHM). Analyte, e.g. glucose molecules, can be predominantly included in a set of objects that transfer more rapidly into the analyte container than other objects, and can have a negligible or zero rate of transfer into the non-analyte container; objects that transfer more rapidly into the non-analyte container can include objects smaller than the analyte or molecules of a set of selected types, including, e.g., sodium chloride. Output light from the containers accordingly includes information about analyte.

21 Claims, 14 Drawing Sheets

(51) Int. Cl.
*A61B 5/145* (2006.01)
*G01N 21/03* (2006.01)
*G01N 21/85* (2006.01)
*G01N 21/39* (2006.01)

(56) References Cited

U.S. PATENT DOCUMENTS

| | | | |
|---|---|---|---|
| 3,973,118 A | 8/1976 | LaMontagne | |
| 4,081,277 A | 3/1978 | Brault et al. | |
| 4,344,438 A * | 8/1982 | Schultz | 600/341 |
| 4,455,089 A | 6/1984 | Yeung et al. | |
| 4,514,257 A | 4/1985 | Karlsson et al. | |
| 4,573,796 A | 3/1986 | Martin et al. | |
| 4,579,430 A | 4/1986 | Bille | |
| 4,721,677 A | 1/1988 | Clark, Jr. | |
| 4,764,670 A | 8/1988 | Pace et al. | |
| 4,822,998 A | 4/1989 | Yokota et al. | |
| 4,957,371 A | 9/1990 | Pellicori et al. | |
| 4,976,542 A | 12/1990 | Smith | |
| 4,981,779 A * | 1/1991 | Wagner | 600/342 |
| 5,080,462 A | 1/1992 | Goto | |
| 5,143,066 A * | 9/1992 | Komives et al. | 600/317 |
| 5,144,498 A | 9/1992 | Vincent | |
| 5,151,585 A | 9/1992 | Siebert | |
| 5,166,755 A | 11/1992 | Gat | |
| 5,218,426 A | 6/1993 | Hall et al. | |
| 5,243,614 A | 9/1993 | Wakata et al. | |
| 5,305,082 A | 4/1994 | Bret | |
| 5,324,401 A | 6/1994 | Yeung et al. | |
| 5,370,842 A | 12/1994 | Miyazaki et al. | |
| 5,394,244 A | 2/1995 | Tsai | |
| 5,414,508 A | 5/1995 | Takahashi et al. | |
| 5,572,328 A | 11/1996 | Fouckhardt et al. | |
| 5,666,195 A | 9/1997 | Shultz et al. | |
| 5,677,769 A | 10/1997 | Bendett | |
| 5,682,038 A | 10/1997 | Hoffman | |
| 5,760,900 A | 6/1998 | Ito et al. | |
| 5,777,329 A | 7/1998 | Westphal et al. | |
| 5,784,507 A | 7/1998 | Holm-Kennedy et al. | |
| 5,792,663 A | 8/1998 | Fry et al. | |
| 5,793,485 A | 8/1998 | Gourley | |
| 5,801,831 A | 9/1998 | Sargoytchev | |
| 5,825,792 A | 10/1998 | Villeneuve et al. | |
| 5,864,641 A | 1/1999 | Murphy et al. | |
| 5,876,674 A | 3/1999 | Dosoretz et al. | |
| 5,880,474 A | 3/1999 | Norton et al. | |
| 5,945,676 A | 8/1999 | Khalil et al. | |
| 5,946,676 A | 8/1999 | Iggulden | |
| 5,953,138 A | 9/1999 | Ellis | |
| 5,982,478 A | 11/1999 | Ainsworth et al. | |
| 6,040,578 A | 3/2000 | Malin et al. | |
| 6,049,727 A | 4/2000 | Crothall | |
| 6,091,502 A | 7/2000 | Weigl et al. | |
| 6,108,463 A | 8/2000 | Herron et al. | |
| 6,122,536 A | 9/2000 | Sun et al. | |
| 6,137,117 A | 10/2000 | Feldstein et al. | |
| 6,169,604 B1 | 1/2001 | Cao | |
| 6,187,592 B1 | 2/2001 | Gourley | |
| 6,192,168 B1 | 2/2001 | Feldstein et al. | |
| 6,216,022 B1 | 4/2001 | Tyrrell et al. | |
| 6,249,346 B1 | 6/2001 | Chen et al. | |
| 6,275,628 B1 | 8/2001 | Jones et al. | |
| 6,285,504 B1 | 9/2001 | Diemeer | |
| 6,295,130 B1 | 9/2001 | Sun et al. | |
| 6,307,623 B1 | 10/2001 | Papuchon et al. | |
| 6,310,690 B1 | 10/2001 | Cao et al. | |
| 6,353,475 B1 | 3/2002 | Jensen et al. | |
| 6,399,405 B1 | 6/2002 | Chen et al. | |
| 6,405,073 B1 | 6/2002 | Crowley et al. | |
| 6,429,022 B1 | 8/2002 | Kunz et al. | |
| 6,438,397 B1 | 8/2002 | Bosquet et al. | |
| 6,459,080 B1 | 10/2002 | Yin et al. | |
| 6,483,959 B1 | 11/2002 | Singh et al. | |
| 6,490,034 B1 | 12/2002 | Woias et al. | |
| 6,505,775 B1 | 1/2003 | Gu et al. | |
| 6,519,037 B2 | 2/2003 | Jung et al. | |
| 6,525,308 B1 | 2/2003 | Schmidt-Hattenberger | |
| 6,558,945 B1 | 5/2003 | Kao | |
| 6,561,978 B1 | 5/2003 | Conn et al. | |
| 6,577,780 B2 | 6/2003 | Lockhart | |
| 6,580,507 B2 | 6/2003 | Fry et al. | |
| 6,584,335 B1 * | 6/2003 | Haar et al. | 600/322 |
| 6,603,548 B2 | 8/2003 | Church et al. | |
| 6,608,679 B1 | 8/2003 | Chen et al. | |
| 6,630,999 B2 | 10/2003 | Shroder | |
| 6,639,679 B2 | 10/2003 | Frojdh | |
| 6,665,113 B2 | 12/2003 | Aso et al. | |
| 6,678,502 B1 | 1/2004 | Zarrabian et al. | |
| 6,694,158 B2 | 2/2004 | Polak | |
| 6,700,664 B1 | 3/2004 | Honda et al. | |
| 6,768,555 B2 | 7/2004 | Lin et al. | |
| 6,781,690 B2 | 8/2004 | Armstrong et al. | |
| 6,785,002 B2 | 8/2004 | Zarrabian et al. | |
| 6,796,710 B2 | 9/2004 | Yates et al. | |
| 6,800,849 B2 | 10/2004 | Staats | |
| 6,809,865 B2 | 10/2004 | Chen | |
| 6,867,420 B2 | 3/2005 | Mathies et al. | |
| 6,867,868 B1 | 3/2005 | Barbarossa | |
| 6,870,149 B2 | 3/2005 | Berezin | |
| 6,887,713 B2 | 5/2005 | Nelson et al. | |
| 6,934,435 B2 | 8/2005 | Kane | |
| 6,952,603 B2 | 10/2005 | Gerber et al. | |
| 6,983,176 B2 | 1/2006 | Gardner et al. | |
| 7,011,630 B2 | 3/2006 | Desai et al. | |
| 7,012,696 B2 | 3/2006 | Orr et al. | |
| 7,016,714 B2 | 3/2006 | Colvin, Jr. | |
| 7,024,236 B2 | 4/2006 | Ford et al. | |
| 7,045,054 B1 | 5/2006 | Buck et al. | |
| 7,046,357 B2 | 5/2006 | Weinberger et al. | |
| 7,064,836 B2 | 6/2006 | Bechtel et al. | |
| 7,130,321 B2 | 10/2006 | Spinelli et al. | |
| 7,135,342 B2 | 11/2006 | Colvin, Jr. et al. | |
| 7,149,396 B2 | 12/2006 | Schmidt et al. | |
| 7,195,465 B2 | 3/2007 | Kane et al. | |
| 7,248,361 B2 | 7/2007 | Kiesel et al. | |
| 7,259,856 B2 | 8/2007 | Kachanov et al. | |
| 7,268,868 B2 | 9/2007 | Kiesel et al. | |
| 7,291,824 B2 | 11/2007 | Kiesel et al. | |
| 7,310,153 B2 | 12/2007 | Kiesel et al. | |
| 7,315,667 B2 | 1/2008 | Schmidt et al. | |
| 7,358,476 B2 | 4/2008 | Kiesel et al. | |
| 7,386,199 B2 | 6/2008 | Schmidt et al. | |
| 7,387,892 B2 | 6/2008 | Kiesel et al. | |
| 7,391,517 B2 | 6/2008 | Trebbia et al. | |
| 7,420,677 B2 | 9/2008 | Schmidt et al. | |
| 7,433,552 B2 | 10/2008 | Kiesel et al. | |
| 7,471,399 B2 | 12/2008 | Kiesel et al. | |
| 7,479,625 B2 | 1/2009 | Kiesel et al. | |
| 7,502,123 B2 | 3/2009 | Kiesel et al. | |
| 7,545,513 B2 | 6/2009 | Kiesel et al. | |
| 7,547,904 B2 | 6/2009 | Schmidt et al. | |
| 7,554,673 B2 | 6/2009 | Kiesel et al. | |
| 7,633,629 B2 | 12/2009 | Kiesel et al. | |
| 7,852,490 B2 | 12/2010 | Kiesel et al. | |
| 7,936,462 B2 | 5/2011 | Jiang et al. | |
| 7,961,326 B2 | 6/2011 | Martini et al. | |
| 8,040,526 B2 | 10/2011 | Kiesel et al. | |
| 8,320,983 B2 | 11/2012 | Martini et al. | |
| 2002/0155485 A1 | 10/2002 | Kao | |
| 2002/0163643 A1 | 11/2002 | Li et al. | |
| 2003/0000835 A1 | 1/2003 | Witt et al. | |
| 2003/0020915 A1 | 1/2003 | Schueller et al. | |
| 2003/0077660 A1 | 4/2003 | Pien et al. | |
| 2003/0137672 A1 | 7/2003 | Moriya et al. | |
| 2003/0161024 A1 | 8/2003 | Zhang et al. | |
| 2003/0189711 A1 | 10/2003 | Orr et al. | |
| 2003/0191377 A1 | 10/2003 | Robinson et al. | |
| 2003/0235924 A1 | 12/2003 | Adams et al. | |
| 2004/0027462 A1 | 2/2004 | Hing | |
| 2004/0031684 A1 | 2/2004 | Witt | |
| 2004/0038386 A1 | 2/2004 | Zesch et al. | |
| 2004/0067167 A1 | 4/2004 | Zhang et al. | |
| 2004/0132214 A1 | 7/2004 | Lin et al. | |
| 2004/0141884 A1 | 7/2004 | Unno et al. | |

(56) References Cited

U.S. PATENT DOCUMENTS

| | | |
|---|---|---|
| 2004/0145738 A1 | 7/2004 | Sun et al. |
| 2004/0175734 A1 | 9/2004 | Stahler et al. |
| 2004/0223135 A1 | 11/2004 | Ortyn et al. |
| 2004/0223881 A1 | 11/2004 | Cunningham et al. |
| 2004/0228375 A1 | 11/2004 | Ghosh et al. |
| 2004/0252957 A1 | 12/2004 | Schmidt et al. |
| 2005/0024636 A1 | 2/2005 | Nakamura |
| 2005/0042615 A1 | 2/2005 | Smith et al. |
| 2005/0068526 A1 | 3/2005 | Avrutsky |
| 2005/0099624 A1 | 5/2005 | Staehr et al. |
| 2005/0124873 A1 | 6/2005 | Shults et al. |
| 2005/0128479 A1 | 6/2005 | Gilbert et al. |
| 2005/0162650 A1 | 7/2005 | Yamamoto |
| 2005/0164320 A1 | 7/2005 | McDevitt et al. |
| 2006/0046312 A1 | 3/2006 | Kiesel et al. |
| 2006/0121555 A1 | 6/2006 | Lean et al. |
| 2006/0138313 A1 | 6/2006 | Tennant et al. |
| 2006/0182659 A1 | 8/2006 | Unlu et al. |
| 2006/0193550 A1 | 8/2006 | Wawro et al. |
| 2006/0268260 A1 | 11/2006 | Liu et al. |
| 2006/0274313 A1 | 12/2006 | Gilbert et al. |
| 2007/0009380 A1 | 1/2007 | Cunningham |
| 2007/0070347 A1 | 3/2007 | Scherer et al. |
| 2007/0076210 A1 | 4/2007 | Kiesel et al. |
| 2007/0116609 A1 | 5/2007 | Baeuerle et al. |
| 2007/0145249 A1 | 6/2007 | Kiesel et al. |
| 2007/0146704 A1 | 6/2007 | Schmidt et al. |
| 2007/0146888 A1 | 6/2007 | Schmidt et al. |
| 2007/0147189 A1 | 6/2007 | Schmidt et al. |
| 2007/0147726 A1 | 6/2007 | Kiesel et al. |
| 2007/0147728 A1 | 6/2007 | Schmidt et al. |
| 2007/0148760 A1 | 6/2007 | Klesel et al. |
| 2007/0201025 A1 | 8/2007 | Greenwald |
| 2008/0013092 A1 | 1/2008 | Maltezos et al. |
| 2008/0013877 A1 | 1/2008 | Schmidt et al. |
| 2008/0128595 A1 | 6/2008 | Kiesel et al. |
| 2008/0181827 A1 | 7/2008 | Bassler et al. |
| 2008/0183418 A1 | 7/2008 | Bassler et al. |
| 2008/0186483 A1 | 8/2008 | Kiesel et al. |
| 2008/0186488 A1 | 8/2008 | Kiesel et al. |
| 2008/0186492 A1 | 8/2008 | Kiesel et al. |
| 2008/0186494 A1 | 8/2008 | Kiesel et al. |
| 2008/0186500 A1 | 8/2008 | Schmidt et al. |
| 2008/0186503 A1 | 8/2008 | Kiesel et al. |
| 2008/0186504 A1 | 8/2008 | Kiesel et al. |
| 2008/0187011 A1 | 8/2008 | Kiesel et al. |
| 2009/0220189 A1 | 9/2009 | Kiesel et al. |

FOREIGN PATENT DOCUMENTS

| | | |
|---|---|---|
| DE | 102007031284 | 1/2009 |
| EP | 1324018 | 7/2003 |
| EP | 1953529 | 8/2008 |
| EP | 1953530 | 8/2008 |
| EP | 1953531 | 8/2008 |
| EP | 1953532 | 8/2008 |
| EP | 1953533 | 8/2008 |
| JP | 04223261 | 8/1992 |
| JP | 550330 | 7/1993 |
| JP | 5240774 | 9/1993 |
| JP | 08261922 | 10/1996 |
| JP | 2004252214 | 9/2004 |
| WO | WO9520144 | 7/1995 |
| WO | WO9944042 | 9/1999 |
| WO | WO0039573 | 7/2000 |
| WO | WO0062050 | 10/2000 |
| WO | WO0201202 | 1/2002 |
| WO | WO0225269 | 3/2002 |
| WO | WO2004063681 | 7/2004 |
| WO | WO2005108963 | 11/2005 |
| WO | WO2006133360 | 12/2006 |
| WO | WO2009015723 | 2/2009 |

OTHER PUBLICATIONS

File History for U.S. Appl. No. 11/315,992, 336 pages.
File History for U.S. Appl. No. 11/316,303, 343 pages.
File History for U.S. Appl. No. 11/702,250, 2012, 191 pages.
File History for U.S. Appl. No. 11/702,325, 549 pages.
File History for U.S. Appl. No. 11/702,329, 495 pages.
File History for U.S. Appl. No. 12/968,115, 138 pages.
File History for EP Application No. 08171499.0 as retrieved from the European Patent Office Electronic System on Nov. 27, 2012, 251 pages.
Wang et al., "An Acetone Breath Analyzer Using Cavity Ringdown Spectroscopy: An Initial Test with Human Subjects Under Various Situations", Meas. Sci. Technol. 19, 2008, 10 pages.
Zirk et al., "A Refractometry-Based Glucose Analysis of Body Fluids", Medical Engineering & Physics, 29, 2007 pp. 449-458.
Zirk et al., "On the Suitability of Refractometry for the Analysis of Glucose in Blood-Derived Fluids", Medical Engineering & Physics, 26, 2004 pp. 473-481.
Adams et al., "Microfluidic Integration on Detector Arrays for Absorption and Fluorescence Mirco-Spectrometers", Sensors and Actuators A 104, 2003, pp. 25-31.
Khalil, "Spectroscopic and Clinical Aspects of Noninvasive Glucose Measurements", Clinical Chemistry, 45:2, 1999, pp. 165-177.
Kondziela, "Accurately Measure Laser Spectral Characteristics", 2006, p. 1.
McNichols et al., "Optical Glucose Sensing in Biological Fluids", an overview, p. 1.
Vogel, "Tuneable Liquid Crystal Fabry-Perot Filters", 2002, p. 1.
2005 "Abstracts of Published Work", dias.umist.ac.uk, 3 pages. (No copy available).
Agilent Technologies, "Agilent 83453B High-Resolution Spectrometer—Technical Specifications", Feb. 2005, pp. 1-8.
Agilent Technologies "Developing Technology: HPLC-Chip/MS", May 25, 2011, 2 pages.
Becker et al., "Polymer Microfabrication Methods for Microfluidic Analytical Applications", Electrophoresis, vol. 21, 2000, pp. 12-26. (abstract only).
Bernini et al., "Silicon Micromachined Hollow Optical Waveguides for Sensing applications", IEEE Journal on Selected Topics in Quantum Electronics, vol. 8, No. 1, Jan./Feb. 2002, pp. 106-110. (abstract only).
Cunningham et al., "Label-Free Assays on the Bind System", Journal of Biomolecular Screening, vol. 9, No. 6, 2004, pp. 481-490.
Devasenathipathy et al., "3 Electrokinetic Flow Diagnostics", in Breuer K.S. Ed. Micro-and Nano-Scale Diagnostic Techniques, Springer Verlag, New York, 2003, pp. 121-166.
Fuhr, Measuring with Light, Sensors Magazine Online, May 2000, 11 pages.
Fuji-Keizai USA, "Biosensor Market, R&D and Commercial Implication", 2004, 5 pages.
Goddard et al., Anti-Resonant Reflecting Optical Waveguides (ARROW), as Optimal Optical Detectors for MicroTAS Applications, dias.umist.ac.uk, 5 pages.
Henry et al., "Wavelength Response of Thin-Film Optical Position-Sensitive Detectors", J. Opt. A: Pure Appl. Opt., Vole. 4, 2002, pp. 527-534. (abstract only).
Johnson et al., "Introduction to Photonic Crystals: Bloch's Theorem, Band Diagrams, and Gaps (But No Defects)", Feb. 3, 2003, 16 pages.
Johnson, "Photonic Crystals: Periodic Surprises in Electromagnetism", printed from ab-initio.mit.edu on Oct. 5, 2006, 29 pages.
Jones et al., "Dielectrophoretic Liquid Actuation Nanodroplet Formation", Journal of Applied Physics, vol. 89, No. 2, 2001, pp. 1441-1448. (abstract only).
Koch et al., "Design and fabrication of a micromachined Coulter counter", J. Micromech. Microeng. 9, 1999, pp. 159-161. (No copy available).

(56) References Cited

OTHER PUBLICATIONS

Law et al., "Low-Voltage Superlattice Asymmetric Fabry-Perot Reflection Modulator", IEEE Phot. Tech. Lett, vol. 3, No. 4, Apr. 1991, pp. 324-326. (abstract only).

Liang et al., "Refractive Index Measurement of Single Living Cell Using a Biophotonic Chip for Cancer Diagnosis Applications", 9th International Conference on Miniaturized Systems for Chemistry and Life Sciences, Oct. 2005, pp. 464-466.

Liu et al., "Nanowell Surface Enhanced Raman Scattering Arrays Fabricated by Soft-Lithography for Label-Free Biomolecular Detections in Integrated Microfluidics", Applied Physics Letters, vol. 87, 2005, pp. 1-3.

Othonos et al. "Fiber-Bragg Gratings—Fundamentals and Applications in Telecommunications and Sensing", Artech House, Norwood, MA, 1999, pp. 304-330 (No copy available).

Prassad, "Introduction to Biophotonics", John Wiley & Sons, Hoboken, N.J. 2003, pp. 311-356. (No copy available).

Sailor, M.J., "Nanostructured Sensors—"Smart Dust"", www.chem.ucsd.edu 2 pages. (No copy available).

Schaefer et al., "Accuracy of Position Detection Using a Position-Sensitive Detector", IEEE Transactions on Instrumentation and Measurement, vol. 47, No. 4, Aug. 1998, pp. 914-919. (abstract only).

Shaw et al., "Optomechanical design of tunable Ip-based Fabry-Perot filters for WDM applications", Journal of Microlithography, vol. 4, Oct.-Dec. 2005, pp. 041303-1-041303-8. (No copy available).

Singh et al., "Analysis of cellular Structure by Light Scattering Measurements in a New Cytometer Design Based on a Liquid-Core Waveguide", IEEE Proceedings Nanobiotechnology, vol. 151, No. 1, Feb. 2004, pp. 10-16. (abstract only).

Singh et al., "Leaky Arrow Waveguides for Optical Chemical and Biosensors", 1998. (No copy available).

Sivaprakasam et al., "Multiple UV Wavelength Excitation and Fluorescence of Bioaerosols", 2nd Joint conference on Point Detections, Williamsburg, VA 2004, 10 pages.

Spear et al., "Low noise position sensitive detector for optical probe beam deflection measurements", Rev. Sci. Instrum., vol. 67, No. 7, Jul. 1996, pp. 2481-2484. (abstract only).

SRU Biosystems, Inc., "BIND Biosensor TM Technology", Apr. 3, 2004 excerpt, 1 page.

Udd, "Good Sense", SPIE's OEMagazine, Aug. 2002, pp. 27-29.

Vollmer et al., "Multiplexed DNA Quantification by Spectroscopic Shift of Two Microsphere Cavities", Biophysical Journal, vol. 85, Sep. 2005, pp. 1974-1979.

Wippich et al., "Tunable and Fiber-Bragg-Grating Sensors", The Industrial Physicist, Jun./Jul. 2003, pp. 24-27. (no copy available).

File History for U.S. Appl. No. 11/702,363, 240 pages.

File History for U.S. Appl. No. 11/702,250, 166 pages.

File History for U.S. Appl. No. 11/316,303, 344 pages.

File History for U.S. Appl. No. 11/702,249, 216 pages.

File History for U.S. Appl. No. 11/315,992, 206 pages.

File History for U.S. Appl. No. 11/316,438, 165 pages.

File History for EP Application No. 08150966.3 as retrieved from the European Patent Office electronic file system on Mar. 18, 2014, 441 pages.

File History for EP Application No. 08151020.8 as retrieved from the European Patent Office electronic file system on Mar. 18, 2014, 257 pages.

File History for EP Application No. 06126524.5 as retrieved from the European Patent Office electronic file system on Mar. 18, 2014, 140 pages.

File History for U.S. Appl. No. 12/098,584, 330 pages.

\* cited by examiner

US 9,307,938 B2

CONTROLLING TRANSFER OF OBJECTS AFFECTING OPTICAL CHARACTERISTICS

RELATED PATENT DOCUMENTS

This application is a continuation of U.S. application Ser. No. 11/957,610 filed Dec. 17, 2007, to issue as U.S. Pat. No. 8,320,983 which is incorporated herein by reference.

This application is related to the following applications, each of which is hereby incorporated by reference in its entirety: U.S. Pat. Nos. 7,358,476; 7,433,552; 7,471,399; 7,502,123; 7,545,513; 7,852,490; and 7,936,463.

BACKGROUND OF THE INVENTION

The present invention relates generally to techniques involving production and use of implantable articles and systems, such as to obtain information about analytes in bodily fluids. More specifically, techniques can control transfer of objects relative to containers in implantable articles and systems.

Various implantable devices have been proposed. For example, U.S. Pat. No. 6,952,603 describes an implantable optical sensing element with a body and with a membrane mounted on the body, defining a cavity. The membrane is permeable to analyte while impermeable to background species. A refractive index element is positioned in the cavity. A light source transmits light of a first intensity onto the refractive element, and a light detector receives light of a second intensity that is reflected from the cavity. A controller device optically coupled to the detector compares the first and second light intensities and relates them to analyte concentration.

It would be advantageous to have improved techniques for implantable articles and systems, including improved techniques for controlling transfer of objects.

SUMMARY OF THE INVENTION

The invention provides various exemplary embodiments, including articles, products, systems, methods, apparatus, and devices. In general, the embodiments involve control of transfer of objects in bodily fluid.

These and other features and advantages of exemplary embodiments of the invention are described below with reference to the accompanying drawings.

DETAILED DESCRIPTION

Figure 1:
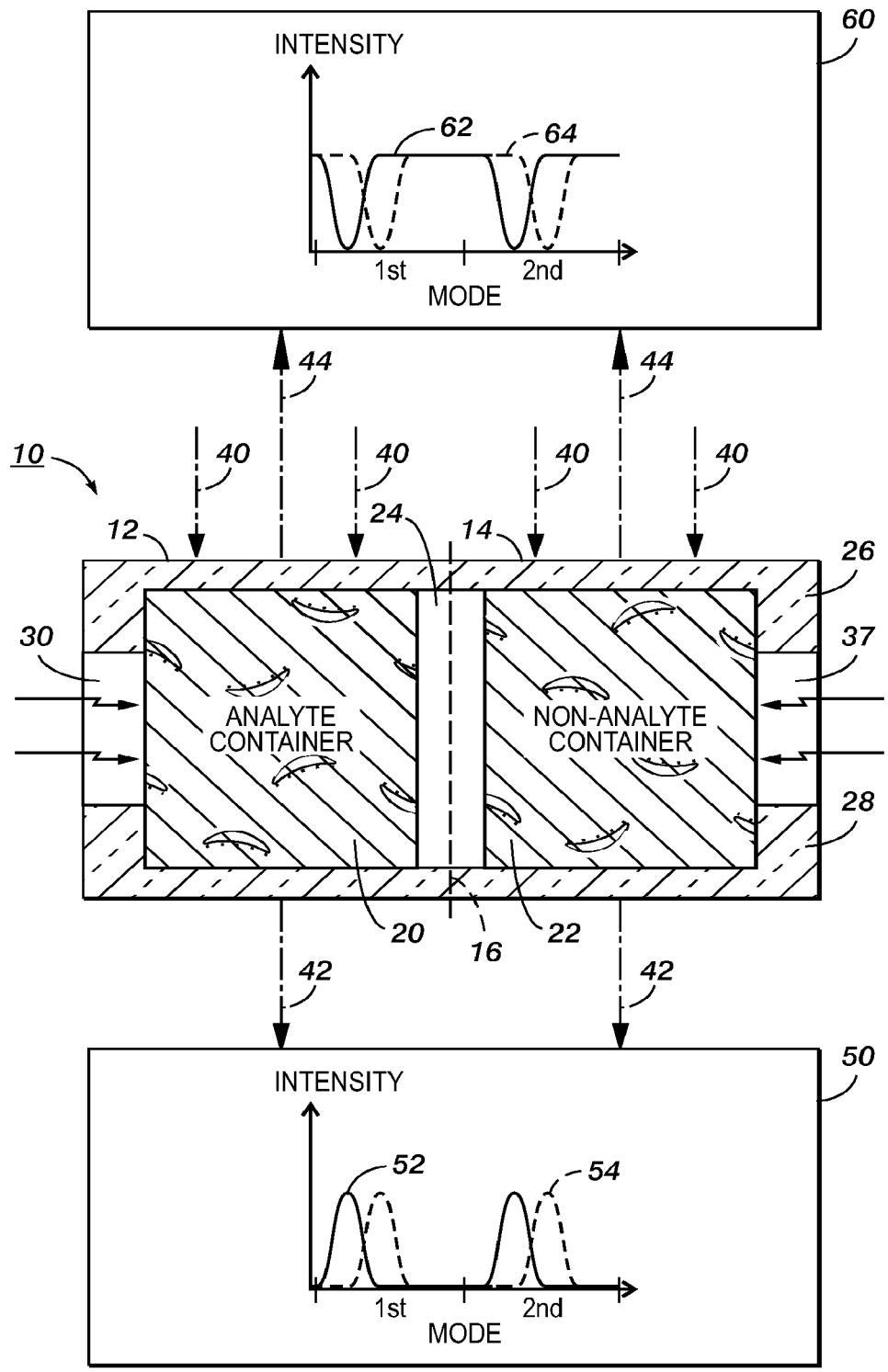
FIG. 1 is a schematic diagram showing optical and fluidic operations of an article that can be implanted in a body.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum.

The various exemplary implementations described below address problems that arise in obtaining information about objects such as molecules in bodily fluids, such as for diagnostic, therapeutic, or other medical purposes. In many contexts, information about only one type of objects is desired, such as about presence or concentration of objects of an analyte type; an example is monitoring or other sensing of glucose, such as in blood or other bodily fluid.

The example of glucose monitoring has great practical significance, because intensive insulin therapy can delay and prevent the progression of microvascular disease in the growing population of diabetic patients. In current insulin therapy techniques, hypoglycemia is the main limiting factor in the glycemic management of insulin-treated diabetic patients—attempts to achieve near-normal glucose levels have reportedly caused a 3.3-fold increase in rate of severe hypoglycemia. Frequent self-monitoring of blood glucose, when integrated with intensive diabetes management, has been shown to improve glycemic control. But patients find it difficult to perform frequent self-monitoring with currently prevalent skin-prick techniques because of associated pain and inconvenience to the patient and invasion of the patient's body that may be upsetting or offensive to others present.

To avoid the need for skin pricks, techniques have been proposed that use implantable structures in which glucose concentration is continuously sensed using an electrochemical reaction. Such techniques are also problematic, however, because they require a wire passing through the skin to connect the device to a transmitter, which can cause infection and therefore limit duration of insertion. In addition, the body continuously reacts to an enzyme required for the electrochemical reaction, which increases device noise. The device also has low sensitivity at low glucose concentrations, where accurate determination of concentration is critical to provide a warning of hypoglycemia onset. Electrochemical reaction products can poison the device reactants, limiting device lifetime.

Other techniques have been proposed in which an implantable structure senses glucose or other objects based on optical characteristics, overcoming some of these problems. The exemplary implementations described below address problems that can arise with implantable structures in which optical characteristics are affected by glucose or other objects in bodily fluid. In many contexts, information about only one type of objects is desired, such as about presence or concentration of objects of an analyte type, while other effects interfere with accurate sensing. It is also possible that information about more than one types of objects is desired. In such contexts, problems can arise in obtaining information specific to one type of objects or to a small number of types of objects, because of presence of other objects or other conditions such as temperature that can also affect optical characteristics.

Glucose Sensing Illustrates these Problems: Even when a sensing system with an implantable structure is sufficiently sensitive to measure glucose changes, it may not be sufficiently specific to be useful because of several factors adversely affecting specificity. Such factors include variations in concentrations of large molecules such as the blood protein Albumin; the physiological variation of Albumin is approximately 1.5 µmol/l, accounting for a change of $1.8*10^{-5}$ in the refractive index of interstitial fluid, as reported by Khalil, O. S., "Spectroscopic and Clinical Aspects of Noninvasive Glucose Measurements", *Clinical Chemistry*, Vol. 45, No. 2, 1999, pp. 165-177. Such factors also include variation in electrolyte concentrations; for example, fluctuation of NaCl concentration (1 mmol/l) results in a $1.1*10^{-5}$ change in interstitial fluid refractive index, as also reported in the above-cited article by Khalil. Such factors also include variation caused by temperature change in index of refraction of water, which constitutes 90% of interstitial fluid; temperature change can account for refractive index change of $1.4*10^{-4}/°$ C. in the physiological temperature range, as can be understood from Weast, R. C., ed., *CRC Handbook of Chemistry and Physics*, $51^{st}$ Ed., Cleveland, Ohio: CRC Press, 1971, p. E-230. In addition to variations in protein concentrations, in electrolyte concentrations, and in temperature of bodily fluid, other factors could interfere with specificity of glucose sensing.

In addressing such problems, some exemplary implementations described below control transfer of objects that affect optical characteristics in an implantable structure. More particularly, in an implantable structure that includes more than one container, some implementations control transfer of objects in bodily fluid differently for different containers. For example, transfer of objects into different containers may be controlled so that glucose is present at a higher concentration in one container than in another, making it possible to obtain glucose-specific information by comparing optical characteristics of different containers.

Also, some exemplary implementations described below address such problems by obtaining additional information. For example, the additional information might relate to electrical conductance of a container's contents; or the further information might relate to optical characteristics of a closed reference container whose contents do not change over time.

Although the exemplary implementations described below can be used to obtain information about analytes or other objects in human bodies, the term "body" is used herein to refer to any living body or a part of such a body that includes fluids, and can include non-human or even non-animal bodies. Fluids that occur in bodies are referred to as "bodily fluids"; common examples of human bodily fluids include blood, lymph, and interstitial fluids, but there are many others.

As used herein, "to implant" a thing in a body refers to any operation that begins with the thing outside the body and ends with the thing at least partially inside the body. An "implantable article" or "implantable product" is therefore any article of manufacture capable of being implanted in a body. An "implantable system" is a system that includes one or more components and that is similarly capable of being implanted in a body.

The term "photon" refers herein to a quantum of light, and the term "photon energy" refers herein to the energy of a photon. Light can be described as having a "photon energy distribution" or, more commonly, a "spectrum", meaning the combination of photon energies that are included in the light; highly monochromatic light, for example, has a photon energy distribution or spectrum with one peak energy value.

Light can also be described as provided by a "light source," which, unless otherwise specified, refers herein to any device, component, or structure that can provide light of the type described; examples of light sources relevant to the below-described implementations include various kinds of pulsed and unpulsed lasers and laser structures, light emitting diodes (LEDs), superluminescent LEDs (SLEDs), resonant cavity LEDs, sources of broadband light that is spectrally filtered such as with a monochromator, and so forth. A "tunable light source" is a light source that provides light with a predominant photon energy that can be changed in response to a signal or operation of some kind.

The term "laser" is used herein to mean any region, element, component, or device in which transitions between energy levels can be stimulated to cause emission of coherent light, such as in the ultraviolet, visible, or infrared regions of the spectrum. A "laser structure" is any structure that includes one or more lasers. A "laser cavity" is a region of a laser in which transitions can be stimulated to cause emission.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where the speed of light in a medium M is a constant $c_M$ less than c, then M has an index of refraction $n_M = c/c_M$.

Where light changes direction in a way that can be illustrated or approximated as a vertex between an incoming ray and an outgoing ray that are both on one side of a surface, the change may be referred to as a "reflection"; similarly, to "reflect" light is to cause the light to change its direction of propagation approximately at such a surface, referred to herein as a "reflection surface". Similarly, where light changes direction in a way that can be illustrated or approximated as a vertex between an incoming ray and an outgoing ray that are on opposite sides of a surface between two media with different indices of refraction, the change may be referred to as a "refraction"; similarly, to "refract" light is to cause the light to change its direction of propagation approximately at such a surface, referred to herein as a "refraction surface". In many practical applications, both reflection and refraction occur at a surface, which may be referred to herein as a "partially reflecting surface".

Where light propagates at less than c, it may be useful to obtain an "optical distance" of propagation; for any segment of length d in which speed of propagation is constant $\epsilon*C$, where $\epsilon=1/n_{EFF}\leq 1$ and $n_{EFF}$ is an effective index of refraction for the segment, optical distance $D(\epsilon)=d/\epsilon$. An optical distance may be referred to herein as an "optical thickness", such as where light is propagating through a thickness of material.

To "photosense" is to sense photons, and to "photosense quantity" of photons is to obtain information indicating a quantity of the photons. Photons that are photosensed are sometimes referred to herein as "incident photons". A surface at which photosensing occurs is referred to herein as a "photosensitive surface".

A "photosensor" is used herein to refer generally to any element or combination of elements that senses photons, whether by photosensing quantity or any other information about the photons. A photosensor could, for example, provide an electrical signal or other signal that indicates results of sensing, such as a signal indicating quantity of incident photons; in general, signals from a photosensor that indicate results of sensing are referred to herein as "sensing results". If electrical sensing events occur in a photosensor in response to incident photons, the photosensor may integrate or otherwise accumulate the results of the electrical sensing events during a time period referred to herein as a "sensing period" or "sense period".

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described. A central wavelength or frequency or other value indicating a central photon energy of a range or subrange is sometimes referred to herein as a "central energy", and may be obtained in various ways, such as by finding an energy that has maximum intensity or that is another type of central value such as a mean or median of the distribution of light within the range or subrange.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In the implementations described below, structures, systems, or parts or components of structures or systems may sometimes be referred to as "attached" to each other or to other structures, systems, parts, or components or visa versa, and operations are performed that "attach" structures, systems, or parts or components of structures or systems to each other or to other things or visa versa; the terms "attached", "attach", and related terms refer to any type of connecting that could be performed in the context. One type of attaching is "mounting", which occurs when a first part or component is attached to a second part or component that functions as a support for the first. In contrast, the more generic term "connecting" includes not only "attaching" and "mounting", but also making other types of connections such as electrical connections between or among devices or components of circuitry. A combination of one or more parts connected in any way is sometimes referred to herein as a "structure".

Some of the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

A structure may be described by its operation, such as a "support structure" that can operate as a support as described above; other examples are defined below. In addition, a structure may be characterized by the nature of its parts or the way in which they are connected; for example, a "layered structure" is a structure that includes one or more layers, and the terms "partial structure" and "substructure" refer to structures that are in turn parts of other structures.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry.

Circuitry can be described based on its operation or other characteristics. For example, circuitry that performs control operations is sometimes referred to herein as "control circuitry" and circuitry that performs processing operations is sometimes referred to herein as "processing circuitry".

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete photosensors or other components produced by other types of processes.

Implementations of ICs described herein include features characterized as "cells" (or "elements") and "arrays", terms that are used with related meanings: An "array" is an arrangement of "cells" or "elements"; unless otherwise indicated by the context, such as for a biological cell, the words "cell" and "element" are used interchangeably herein to mean a cell or an element of an array. An array may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

An IC includes a "photosensor array" if the IC includes an array of cells, and at least some of the cells include respective photosensors. A cell that includes a photosensor may also include "cell circuitry", such as circuitry that makes connections with the photosensor, that transfers signals to or from the photosensor, or that performs any other operation other than photosensing. In general, a cell's photosensor and cell circuitry are within a bounded area of the array, an area sometimes referred to herein as the "cell's area". The part of a cell's area in which an incident photon can be photosensed is referred to herein as "sensing area".

In an application of an IC that includes a photosensor array, circuitry that "responds to" one or more photosensors can be any circuitry that, in operation, receives information from the photosensors about their photosensing results through an electrical connection. Circuitry that responds to a photosensor could be circuitry in the same cell as the photosensor, or it could be array circuitry, peripheral circuitry, or other external circuitry, or it could include any suitable combination of cell circuitry, array circuitry, peripheral circuitry, and other external circuitry. Circuitry that responds to a photosensor could employ any suitable technique to readout photosensing results, including, for example, CCD, CMOS, or photodetector array (PDA) techniques.

An IC is or includes a "position-sensitive detector" or "PSD" if it includes a substantially continuous photosensitive surface and it provides electrical signals indicating a position resulting from a pattern of incident light on the photosensitive surface. For example, the signals could be two currents whose normalized difference is proportional to a centroid of the incident light pattern.

FIG. 1 schematically illustrates general features of product 10, an example of an implantable article or product that can be implemented in various ways as described in greater detail below. As with other exemplary implementations described below, product 10 involves a combination of parts or components. For example, product 10 includes parts 12 and 14, which could be referred to herein as first and second parts or as analyte and non-analyte parts. In the illustrated implementation, parts 12 and 14 are connected along dashed line 16, which can be the result of being fabricated together.

Parts 12 and 14 includes containers 20 and 22, respectively, illustratively connected in a structure that includes wall-like parts 24, 26, and 28, with wall-like part 28 connecting parts 24 and 26 and being between containers 20 and 22. The respective boundary of each of containers 20 and 22 illustratively includes one or more bounding regions through which objects in bodily fluid can transfer between interior and exterior of the container, i.e. can enter and/or exit. Such bounding regions are sometimes referred to herein as "object transfer regions", in contrast with bounding regions that are closed; a closed or sealed container would have no object transfer regions on its boundary, as illustrated below in relation to some exemplary implementations. Although object transfer regions could have any shape and could include any appropriate structures through which objects can transfer, the net effect of all such object transfer regions is summarized for container 20 by opening 30 and for container 22 by opening 32; in exemplary implementations described below, containers may have any suitable number of object transfer regions, which may include various fluidic components that permit diffusion and flow of objects and perform filtering, pumping, and so forth.

Each of parts 12 and 14 is also operable as a respective optical cavity. The term "reflective optical cavity", or simply "optical cavity" or "cavity", refers herein to a light-transmissive region that is at least partially bounded by light-reflective components, with the light-reflective components and the light-transmissive region having characteristics such that a measurable portion of light within the light-transmissive region is reflected more than once across the light-transmissive region. An "optical cavity component" is a component that includes one or more optical cavities.

In the exemplary implementation of FIG. 1, each part's optical cavity operation can arise in a respective light-transmissive region between light-reflective regions (not shown) of wall-like parts 24 and 26. The respective light-transmissive region of part 12 can include at least part of analyte container 20, and that of part 14 can similarly include at least part of non-analyte container 22. Therefore product 10 includes an "optical cavity structure", meaning a structure with parts or components that can operate as an optical cavity.

In operation as optical cavities, each of parts 12 and 14 can illustratively receive input light through a surface of wall-like part 24 as indicated by arrows 40 and can provide transmitted output light through a surface of wall-like part 26 as indicated by arrows 42 and reflected output light through a surface of wall-like part 24 as indicated by arrows 44. The surfaces through which input light is received (sometimes referred to as "entry surfaces") and through which output light is transmitted or reflected (sometimes referred to as "exit surfaces") can, however, be somewhat arbitrary, and it may be possible in some implementations to reverse direction of input and output light or to have multiple entry or exit surfaces; the term "light interface surface" is therefore used herein as a generic term that includes any of these types of entry and exit surfaces.

As suggested in FIG. 1, light interface surfaces of the first and second parts 12 and 14 can be aligned so that they can receive input light from the same light source (not shown) and can similarly provide output light to the same photosensing component (not shown), whether photosensing output light from transmission modes or reflection modes; other possible implementations are described below. In general, light interactive surfaces are "aligned" in a given application with one or both of an external light source and an external photosensing component if they are in approximately the same plane or other surface such that input light from the application's external light source is received similarly on both surfaces and/or output light to the application's photosensing component is provided similarly from both surfaces.

Within the broad category of optical cavities, there are various more specific types: For example, a "transmissive cavity" can operate, in response to input light from one or more external light sources at an entry surface, providing a transmitted portion of its output light at an exit surface different than the entry surface (a complementary, reflected portion may be provided at the entry surface); a "Fabry-Perot cavity" is a reflective optical cavity in which constructive interference (or positive reinforcement) occurs in one or more photon energy subranges while destructive interference occurs in others.

A Fabry-Perot cavity or other optical cavity that can operate to provide output light in one or more photon energy subranges while not providing output light with other photon energies may be described as having one or more "modes", each for a respective one of the output light energy subranges; if the cavity is a transmissive cavity, modes of its transmitted output light may be referred to as "transmission modes" and modes of its reflected output light may be referred to as "reflection modes". In the reflection spectrum, either the valley-like dips or the plateau-like reflection bands between the dips can be considered as "reflection modes". An emitting cavity can be described as "stimulated at" a mode by any operation that results in emission of output light in the mode's photon energy subrange. Similarly, a transmissive cavity can be described as "illuminated at" a mode by any operation that provides input light that results in transmission or reflection of output light in the mode's photon energy subrange.

In typical implementations of optical cavities, two light-reflective components have approximately parallel reflection surfaces and the light-transmissive region is sufficiently uniform that measurements would indicate many reflections of light within the light-transmissive region. Such cavities define a directional orientation as follows: Directions in which light could propagate and be reflected many times within the light-transmissive region are referred to herein as "reflection directions", and generally include a range of directions that are approximately perpendicular to both reflection surfaces. Directions that are approximately parallel to both reflection surfaces, on the other hand, are generally referred to herein as "lateral directions". In addition, the terms "in", "inward", or "internal" generally refer to positions, directions, and other items within or toward the light-transmissive region between the reflection surfaces, while "out", "outward", and "external" refer to positions, directions, and other items outside or away from the light-transmissive region. In general, it should be understood that the above directional orientation is arbitrary and only for ease of description, and that an optical cavity may have any appropriate orientation.

The above directional orientation does not in general apply to angle of incidence of input light. Transmissive cavities can typically operate in response to incident light that is not perpendicular to entry surfaces or reflection surfaces. Light incident on a transmissive cavity's entry surface at any angle is reflected multiple times within the cavity, producing transmission modes in accordance with the cavity's geometry. But transmission modes are affected by angle of incidence: Depending on the type of cavity and the angle of incidence, modes can be red shifted in comparison to perpendicular incidence; if all light enters a cavity at approximately the same angle, performance is affected only by the shifting of modes and modes are not also broadened, but performance is reduced if a cavity receives incident light distributed across a large angular range because transmission mode structure is then averaged over multiple angles.

The term "object" is used herein in the general sense of any thing that can affect an optical characteristic, whether a characteristic of emission (e.g. radiation, fluorescence, incandescence, luminescence, etc.), scattering (e.g. reflection, deflection, diffraction, refraction, etc.), or other types of light transmission. The optical characteristic is "affected by presence of" or is simply "affected by" the object.

Examples of objects that could occur in implementations as described below include droplets, small volumes of fluid, single molecules, agglomerated molecules, molecule clusters, cells, viruses, bacteria, proteins, DNA, microparticles, nanoparticles, and emulsions. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be a "scattering component" of a droplet. An analyte (i.e. a chemical species being investigated) in a droplet can act as a fluorescent, absorbent, or scattering component.

Some implementations as described below involve groups of objects that are treated as interchangeable because of some shared characteristic, with such a group of objects being referred to herein as a "type" of objects. For example, all molecules that satisfy a criterion for being glucose molecules can be treated as the same type of objects, i.e. the type "glucose". More generally, all objects that are examples of a chemical species being investigated are examples of an "analyte type".

A type of objects is "present in", "positioned in", or simply "in" an optical cavity when a sufficient quantity of objects of the type are in all or some part of the cavity's light-transmissive region to have a measurable effect on an optical characteristic of the optical cavity. An optical cavity provides "object-affected output light" if the optical cavity's output light is different in some way when a type of objects is present in the cavity than when the type of objects is absent, with the difference being due to the effect of the type of objects on the cavity's optical characteristics.

Figure 2:
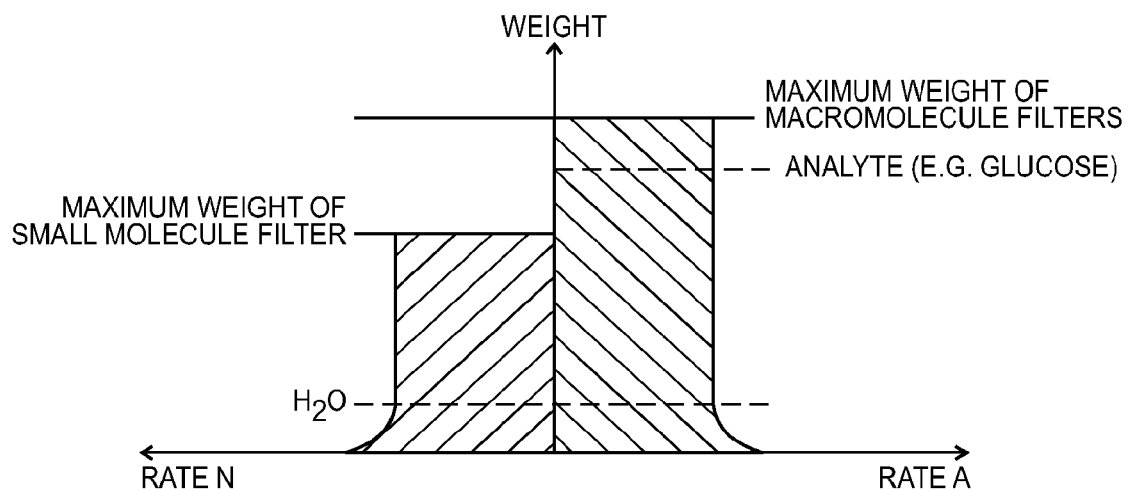
FIG. 2 is a graph showing exemplary rates of transfer of objects into containers in an article operating like that in FIG. 1.
Figure 3:
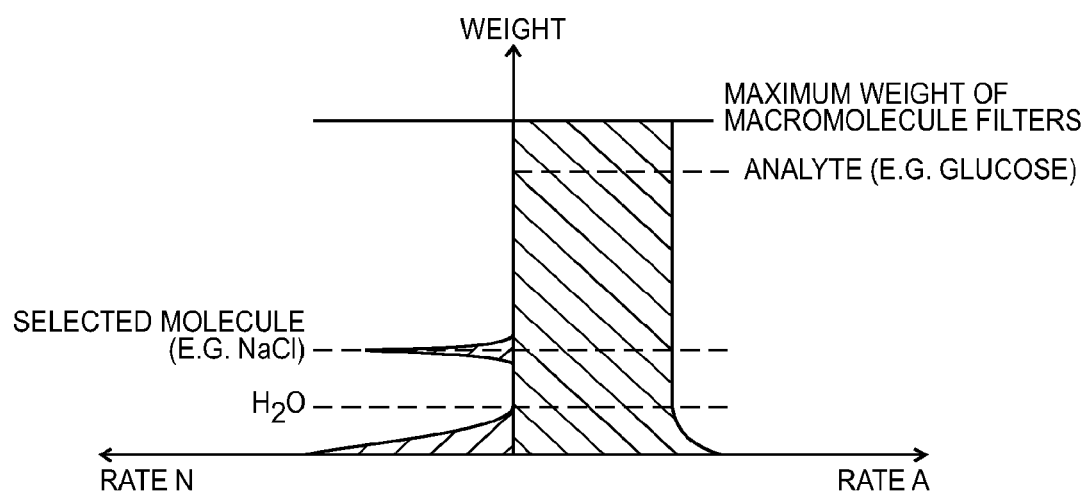
FIG. 3 is another graph showing exemplary rates of transfer of objects into containers in an article operating like that in FIG. 1.

The graphs in FIGS. 2 and 3 illustrate and compare rates of transfer of objects between exterior and interior of containers 20 and 22. An object "is transferred" or "transfers" between a container's exterior and interior if the object moves between the container's exterior and interior by entering and/or exiting at least once. For example, the object could be conveyed between exterior and interior by flow of a bodily fluid in response pressure from a pump or other pressure source, in which cases the object may be referred to as being "carried" by the bodily fluid; or the object could be conveyed between exterior and interior as a result of diffusion due to a concentration gradient of objects of its type in a bodily fluid, in which case the object may be referred to as "diffusing" in the bodily fluid.

Various techniques can be used to control rates of transfer of objects that are carried or diffusing in bodily fluid, and several such techniques are described below. In general, control techniques can cause different types of objects to be transferred at different rates. The graphs in FIGS. 2 and 3 each illustrate a technique in which rates of transfer are controlled differently for container 20, shown on the right of the vertical axis as "RateA", than for container 22, shown on the left of the vertical axis as "RateN". The rates are ordered along the vertical axis by object weight, such as molecular weight.

Transfer rates could be measured along the leftward and rightward horizontal axes with any appropriate units, such as weight per unit time or number of objects per unit time, with the curves shown being merely illustrative of possible rates that could be obtained. In comparing rates, therefore, a first rate is "more rapid" than a second rate if the first rate is farther from the vertical axis, either leftward or rightward, than the second rate. Conversely, a first rate is "slower" than a second rate if the first rate is closer to the vertical axis than the second rate. In any case, a rate so slow that it is not measurable or, in the context of other rates occurring relative to the same container, is negligible, appears on or close to the vertical axis; such rates are sometimes referred to herein as "zero rates" or "negligible rates", while other rates are referred to as "non-zero rates".

In each graph, the rightward RateA curve shows non-zero rates of transfer of a first set of objects, i.e. a first set of types of objects, that are lighter than a maximum weight permitted to pass by large object filters, sometimes referred to herein as "macromolecule filters"; the portion of each rightward curve above the maximum weight shows zero or negligible rates of transfer of other objects, i.e. objects of types that are heavier than the maximum weight and therefore not in the first set. Similarly, the leftward RateN curve in each graph shows non-zero rates of transfer of a second set of objects, i.e. a second set of types of objects: In FIG. 2, the second set similarly includes objects that are lighter than a maximum weight permitted to pass by small object filters, meaning filters that only permit objects below the maximum weight to pass; in FIG. 3, on the other hand, the second set includes, other than very light objects at or below the weight of water, only one specific type of molecule such as sodium chloride (NaCl), referred to herein as a "selected molecule" or "selected type", which could be selected by a filter referred to herein as a "selective filter". A similar technique could be implemented for a set of selected types of molecules including any suitable combination of, e.g. sodium chloride, calcium carbonate, magnesium carbonate, or other electrolytes and possibly other molecule types; it is worth noting that filters for such electrolytes are expected to permit very rapid transfer of selected type of molecules. Both leftward RateN curves also show, of course, zero or negligible rates of transfer of other objects, i.e. objects of types that are not in the second set.

Each graph illustrates a possible relationship of types of objects in the first and second sets. As can be seen by comparing the leftward and rightward curves in each graph, the intersection of the first and second sets includes a shared subset of objects, i.e. of objects that have both non-zero RateA and non-zero RateN, while the remainder of the first set includes a non-shared subset of objects, i.e. of objects that have non-zero RateA but a zero or negligible RateN. In the illustrated examples, the remainder of the second set, i.e. objects of types that are in the second set but not the first set, is an approximately empty subset, meaning that very few if any types of objects are in this subset; in other words, none of the objects with non-zero RateN have zero or negligible RateA. Finally, objects of an analyte type such as glucose have a non-zero RateA in both graphs but a zero or negligible rate RateN in both graphs, and are therefore predominantly in the non-shared subset; objects of a given type are referred to herein as "predominantly" in a set or subset if the majority of objects of the given type are in the set or subset.

As a result of different rates of transfer as shown in FIGS. 2 and 3, parts 12 and 14 in FIG. 1 have different optical characteristics when operating as optical cavities. Box 50 at the ends of arrows 42 contains a graph, illustrating that the optical cavities of the first and second parts 12 and 14 each have a set of transmission modes in which they transmit output light, with intensity functions of two transmission modes of non-analyte container 22 being illustrated by solid-line curve 52 and those of counterpart modes of analyte container 20 being illustrated by dashed-line curve 54. Similarly, box 60 at the ends of arrows 44 contains a graph, illustrating that the optical cavities of the first and second parts 12 and 14 each have a set of reflection modes in which they reflect output light, with intensity functions of two reflection modes of non-analyte container 22 being illustrated by solid-line curve 62 and those of counterpart modes of analyte container 20 being illustrated by dashed-line curve 64.

The term "intensity function" refers to a function that relates intensity of output light to another parameter, such as photon energy for an "intensity-energy function" or, in some implementations, position of a light interface surface or a photosensitive surface. An intensity function can have any of a wide variety of shapes and features, but a shape that frequently arises in transmission modes is the "peak", a shape characterized by a maximum value from which a curve for the function slopes steeply downward. Peaks have various features, including "central value", meaning the value of the other parameter at which the peak's maximum occurs, such as "central energy" for an intensity-energy function; "maximum intensity" or simply "maximum" or "amplitude", meaning the intensity value at the peak's maximum, whether measured as an absolute intensity or relative to another feature, such as a nearby minimum value; "contrast", meaning a value indicating relationship between magnitudes of the peak's maximum intensity and of one or more nearby minima of the transmission intensity function; and "intermediate intensity width", meaning the width of the peak at an intensity somewhere between its maximum and nearby minima, such as a full width half maximum (FWHM). Reflection modes have similar features, though typically with valley-like dips, sometimes referred to as "valleys", and plateau-like reflection bands between the valleys, approximately complementary to the counterpart transmission modes; therefore, each valley in the reflection intensity function has a central energy and an FWHM similar to those of the counterpart peak in the transmission intensity function.

Features such as transmission mode peaks and reflection mode valleys are examples of optical characteristics and, more specifically, "optical spectrum characteristics", "optical spectrum features", or simply "spectrum characteristics", meaning that they appear in functions such as intensity-energy functions that depend on photon energy, represented in boxes 50 and 60 by the horizontal axes indicating, e.g., wavelength or frequency; positions on such axes may be referred to as "spectral positions". As shown in FIG. 1, the central energies of the peaks and valleys are displaced along the respective horizontal axes between spectral positions, i.e. between curves 52 and 54 in box 50 and between curves 62 and 64 in box 60. These displacements or "shifts" are caused by differences in contents of containers 20 and 22, resulting from rates of transfer that are controlled, such as in one of the ways illustrated in FIGS. 2 and 3. More specifically, they result from certain objects that affect the spectrum characteristics, including analyte and various others. An object that affects a spectrum characteristic of an optical cavity is sometimes referred to herein as a "spectrum-affecting object". Output light from an optical cavity that is affected by a spectrum-affecting object is sometimes referred to herein as "spectrum-affected". Similarly, the term "shift" refers herein to any displacement of a spectrum characteristic or feature with respect to photon energy, e.g. wavelength, frequency, or phase; a "spectrum-shifting object" shifts a spectrum characteristic or feature, e.g. with respect to wavelength, frequency, or phase; and cavity output light in which a spectrum characteristic or feature is shifted is "spectrum-shifted".

In general, information can be encoded in one of these features not only in shifts but also in various other ways, including, for example, absorption effects such as reduced maximum intensity or contrast or increased intermediate intensity width, e.g. full width half maximum (FWHM); encoding 10 techniques involving such effects are described in co-pending U.S. Pat. No. 7,545,513 and incorporated herein by reference in its entirety. Once encoded, such information can also be recovered in various ways, including those described in co-pending U.S. Pat. No. 7,502,123 and incorporated herein by reference in its entirety.

As a result of these features, product 10 can be used in applications in which optical characteristics affected by contents of analyte container 20 are compared with those affected by contents of non-analyte container 22. Furthermore, product 10 can be implanted within the body, allowing bodily fluid to enter and exit from containers 20 and 22, such as from blood, lymph, or interstitial fluid, and continuous monitoring is possible if fluid is continuously transferred in this manner.

The general features in FIG. 1 could be implemented in many ways, as exemplified by the various implementations described below. Parts of product 10 could be made of any of a wide variety of materials in various shapes and sizes and using a wide variety of different fabrication techniques. Further, connections between parts 12 and 14 and between other parts could be made in a wide variety of ways using various connecting techniques, including various deposition, coating, bonding, adhesive, or other connecting techniques.

The curves in boxes 50 and 60 in FIG. 1 are typical of intensity-energy curves that could be obtained from operation of a "homogeneous optical cavity", meaning a cavity whose light-transmissive region includes an extended part with substantially constant optical distance between its reflection surfaces. Each curve is an intensity-energy graph or "output spectrum" for the respective optical cavity's operation.

Each of the transmission mode peaks could be referred to as an "intensity-energy peak" or simply "intensity peak" that results from a respective transmission or reflection mode. The maxima of intensity-energy peaks (and minima of the counterpart reflection mode valleys) are spaced apart as a function of photon energy (e.g. wavelength), and the difference between the central energy of adjacent transmission mode peaks is referred to as "free spectral range" or "FSR".

The wavelength $\lambda$ of each intensity-energy peak can be obtained from $\lambda(k)=2nd/k$, where n is the refractive index of the cavity, d is cavity thickness, and k is a non-zero integer. Therefore, if refractive index of the cavity changes, $\lambda(k)$ also changes for a given value of k, so that if a peak's central energy changes, as indicated by $\Delta\lambda+$ and $\Delta\lambda-$ for peak 134, the change provides information about refractive index change. Similarly, the intensity of the peaks depends on absorption in the cavity, so that if the intensity of a peak departs from its maximum, the change provides information about absorption change.

In general, the exemplary implementations described herein operate as homogeneous optical cavities, but similar techniques should in principle be applicable to products in which each part can be operated as an "inhomogeneous optical cavity", meaning a cavity that does not meet the above definition of a homogeneous optical cavity. In general, further information about homogeneous and inhomogeneous optical cavities and about techniques for encoding information in their optical characteristics is provided in co-pending U.S. Pat. No. 7,545,513 and incorporated herein by reference in its entirety.

Various techniques can be used to produce laterally varying energy distributions with inhomogeneous optical cavities having laterally varying optical thicknesses and, even with homogeneous optical cavities, with angled illumination from a point light source rather than perpendicular illumination; several techniques are described in U.S. Pat. No. 7,291,824, incorporated herein by reference in its entirety.

Figure 4:
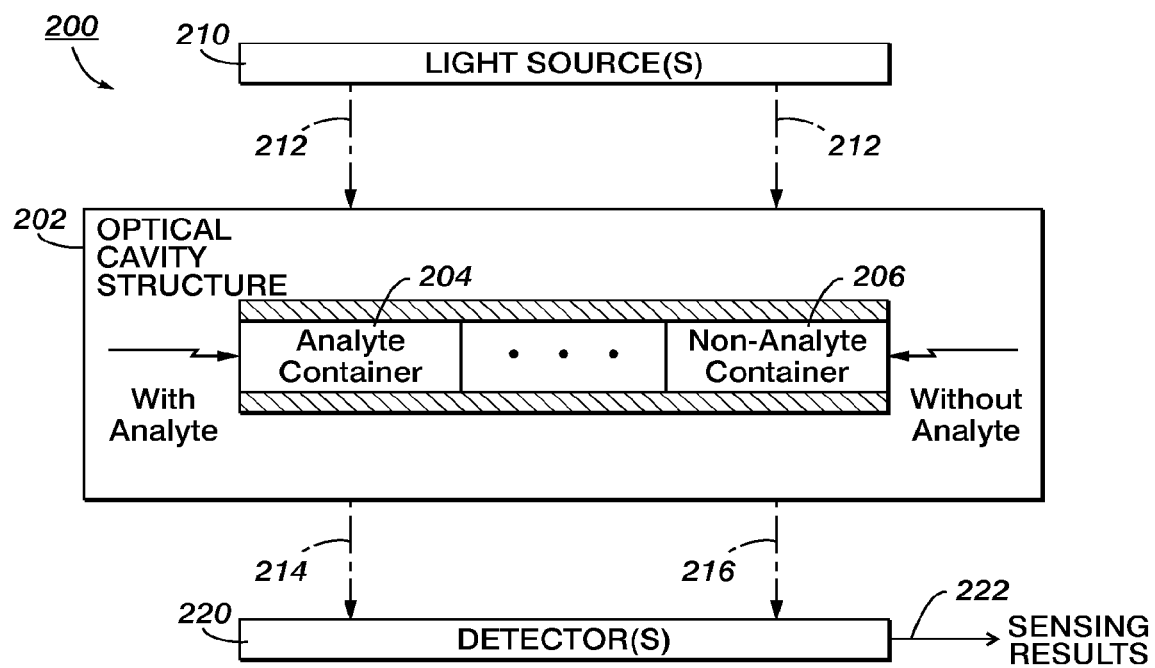
FIG. 4 is a schematic diagram of an implementation of a system that can include an article as in FIG. 1.

FIG. 4 shows system 200, an exemplary implementation of a system that can include a product with features of product 10 in FIG. 1. As used herein, a "system" is a combination of two or more parts or components that can perform an operation together. A system may be characterized by its operation: for example, an "analyte information system" is a system that operates somehow on analyte information; a "processing system" is a system that performs data or signal processing; and so forth.

Within a system, components and parts may be referred to in a similar manner. One component of an analyte information system in which information is obtained about an analyte's optical characteristics, for example, can be a "detector component" or simply "detector", meaning a component that detects light; similarly, a "light source component" includes one or more light sources; an "optical component" performs an optical operation; a "photosensing component" performs a photosensing operation; an "information obtaining component" obtains information, such as from photosensing results; an "adjusting component" performs an adjusting operation, such as on photosensing results; a "light source component" includes one or more light sources; a "light-transmissive component" or simply "transmission component" transmits light; a "light-reflective component" or simply "reflective component" reflects light; in contrast, a "reflection component" includes one or more light-reflective components and operates to reflect, e.g. incident, input, output, or exiting light from an article, device, or system; and other examples are defined further below. Other parts or components can be characterized by their structure.

System 200 includes optical cavity structure 202, a structure that can include two or more containers, each operable in a respective optical cavity and with features described above. In system 200, a set of objects that include analyte can be transferred into analyte container 204, while a set of objects that does not include analyte can be transferred into non-analyte container 206, and there can be one or more other containers between containers 204 and 206, as in some of the exemplary implementations below.

In operation, light source component 210 provides incident light, represented by arrows 212, to structure 202, causing optical cavity operation in at least the respective parts that include containers 204 and 206. The presence of a set of spectrum-affecting objects with analyte in container 204 affects the output light provided by structure 202, and the spectrum-affected output light, represented by arrow 214, can then be photosensed within detector component 220. Similarly, the presence of a set of spectrum-affecting objects without analyte in container 206 affects the output light provided by structure 202, with spectrum-affected output light, represented by arrow 216, also being photosensed within detector component 220 but with the sensing results from containers 204 and 206 being different, e.g. with shifted or displaced features.

Detector component 220 could be implemented in many ways in various implementations. For example, detector component 220 may include a photosensing component such as an IC photosensing array or a position-sensitive detector (PSD) with one or more photosensitive surfaces at which intensity is detected. In most implementations, an appropriate combination of light sources and detectors is desirable. Minimally, component 210 could include a single laser light source that concurrently or alternately illuminates containers 204 and 206 and detector component could include a single discrete photosensor that receives light from both of containers 204 and 206. In general, however, current implementations include a respective detector for each container, which allows simpler signal processing. As mentioned below in relation to some examples, it may also be appropriate to spread or otherwise modify laser light or to provide uniform illumination of an optical cavity's entry surface in another way to obtain optical cavity operation across an appropriately large portion of a container, in turn providing output light across the cavity's exit surface.

The sensing results from detector component 220 can be provided to other components within system 200 or to external components, as represented by arrow 222. Sensing results could then be used in a variety of ways, before or after conversion from analog to digital values, to obtain information about analyte, such as presence, concentration, or other characteristics.

In implementations with inhomogeneous optical cavities and with shifts in intensity-position functions, detector component 220 could be implemented in other ways, such as with a photosensing IC, as described in co-pending U.S. Pat. No. 7,471,399 and incorporated by reference herein in its entirety. The implementation in FIG. 4 might, however, alternatively be implemented with photosensing components that do not include photosensing ICs, such as with one or more discrete photodiodes.

Although in general structure 202 can be operated with any suitable type of optical cavity, including an emitting cavity or a transmissive cavity, FIG. 4 illustratively shows light component 210 as including one or more light sources that can be included within system 200 to illuminate one or more parts of structure 202, such as to operate as transmissive, homogeneous optical cavities. In this case, the output light represented by arrows 214 and 216 could include one or both of transmitted and reflected light.

Figure 5:
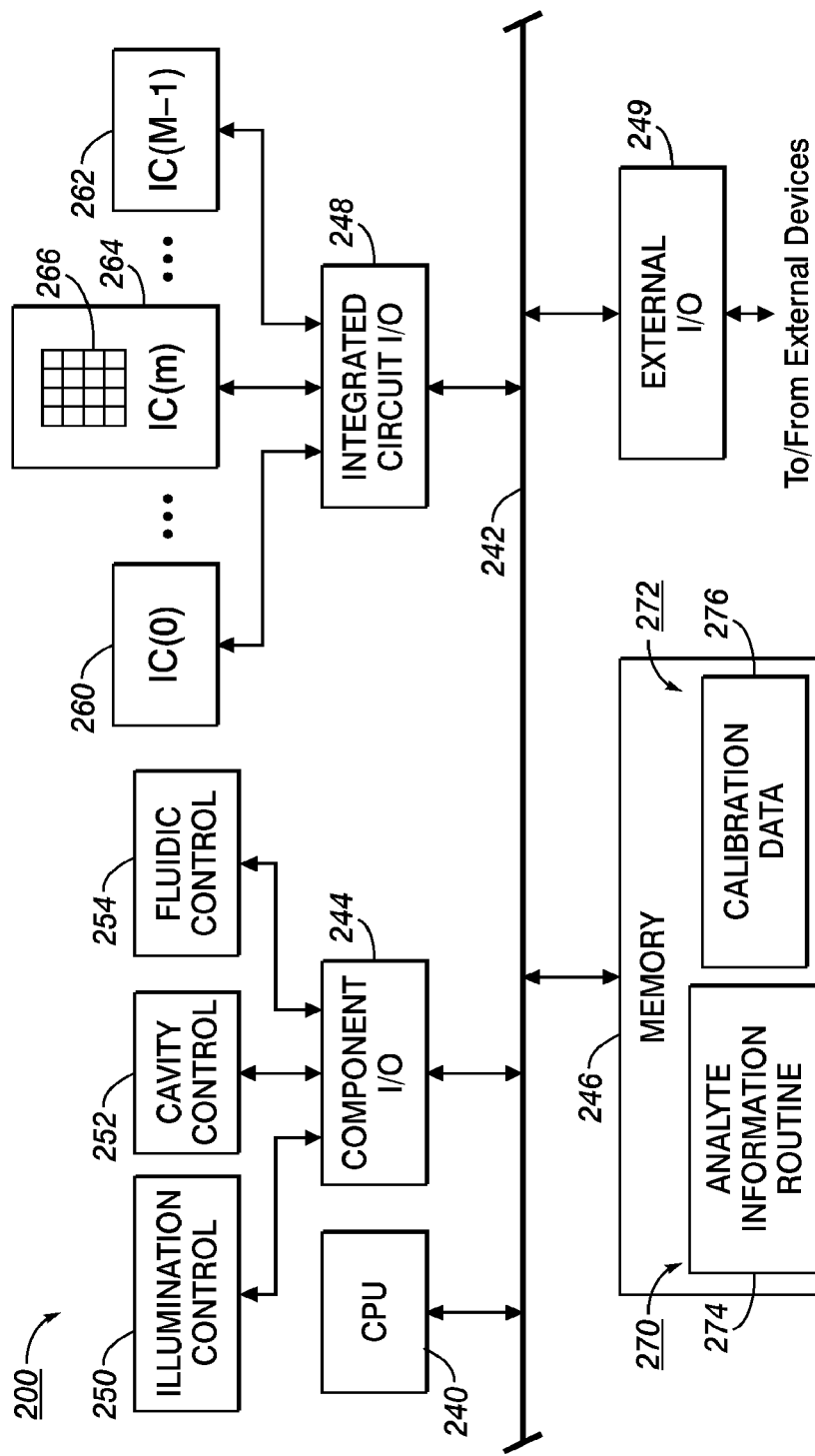
FIG. 5 is a schematic circuit diagram of an implementation of a system with components like that in FIG. 4.

FIG. 5 illustrates electrical components that can be used in implementing system 200 as in FIG. 4. System 200 illustratively includes central processing unit (CPU) 240 connected to various components through bus 242, but a wide variety of other architectures could be employed, including any appropriate combination of hardware and software, as well as specialized hardware components such as application specific integrated circuits (ASICs) for one or more of the illustrated components or in place of a software component executed by CPU 240.

System 200 also includes component input/output (I/O) component 244, memory 246, integrated circuit input/output (IC I/O) 248, and external I/O 249, all connected to bus 242. System 200 can include various other components (not shown) connected to bus 242. In addition to connections through external I/O 249 by which signals can be provided to and received from external devices, bus 242 can also be connected directly to components outside of system 200.

Component I/O 244 permits CPU 240 to communicate with certain components of system 200, illustratively including illumination control 250, cavity control 252, and fluidic control 254. For interactive applications, component I/O 244 could also be connected to a suitable user interface, such as a monitor and keyboard (not shown). In the exemplary implementation in FIG. 5, illumination control 250 can include light sources 220 (FIG. 4) and circuitry for controlling them; cavity control 252 can include electrodes or other components that can be operated to control cavity 204 and other cavities and can also include circuitry connected to those components; and fluidic control 254 can similarly include pumps or other fluidic devices or components that can operate to modify fluidic transfer into, through, or out of one or both of containers 204 and 206, and can also include circuitry connected to those devices and components.

In the illustrated implementation of system 200, IC I/O 248 is a similar I/O component that permits CPU 240 to communicate with one or more ICs, such as in detector 220 in FIG. 4. M ICs are illustrated by a series from IC(0) 260 to IC(M−1) 262, including IC(m) 264 with a photosensor such as a single discrete photosensor or with exemplary array 266.

Memory 246 illustratively includes program memory 270 and data memory 272, although instructions for execution by CPU 240 and data access during execution of instructions could be provided in any suitable way, including through external devices or components. The routines stored in program memory 270 illustratively include analyte information routine 274. In addition, program memory 270 could store various additional routines and also subroutines (not shown) that CPU 240 could call in executing routine 274. Similarly, the data in data memory 272 illustratively include calibration data 276, but could include various additional items of data and data structures accessed by CPU 240.

In executing routine 274, CPU 240 can provide signals to cavity control 252 and to analyte control 254 so that an analyte is present in cavity 204, for example, with the analyte having optical characteristics that affect output light from cavity 204. CPU 240 can also provide signals to illumination control 250 so that cavity 204 is appropriately illuminated to provide spectrum-affected output light. CPU 240 can also provide signals to each of ICs 260 through 262 to obtain sensing results that include information about the analyte in cavity 204. In an implementation with a position-sensitive detector (PSD), CPU 240 could instead provide whatever signals are necessary to obtain photosensed quantities from the PSD; for example, CPU 240 could control circuitry to connect output currents from the PSD to a differential amplifier.

Figure 6:
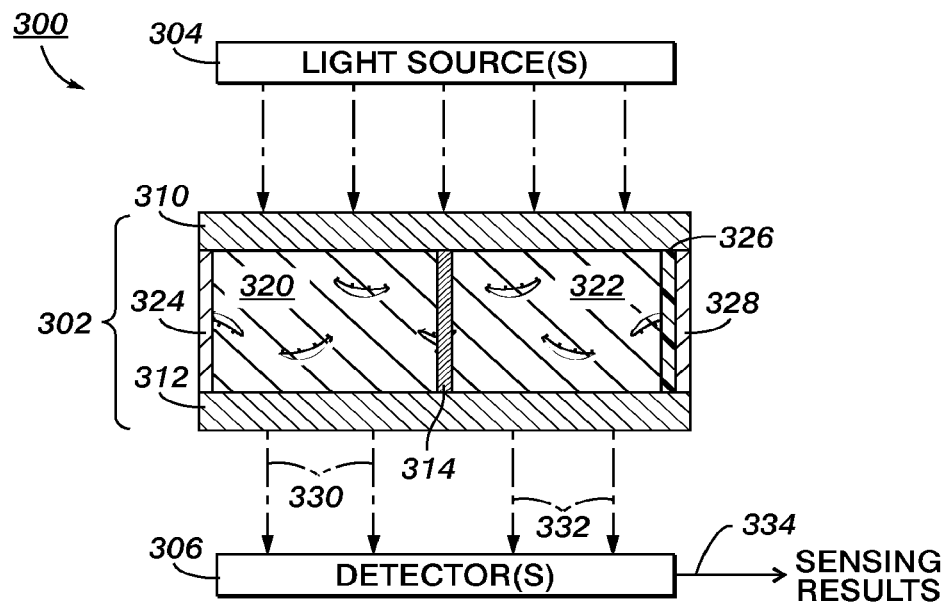
FIG. 6 is a schematic diagram similar to FIG. 4, but with a cross section of an optical cavity structure.

FIG. 6 illustrates application of a system as described above in relation to FIGS. 4 and 5 in which optical cavity structure 202 (FIG. 4) is included in an implantable glucose sensing product with features as described above in relation to FIG. 1, in which case cavity control 252 (FIG. 5) would typically be unnecessary. System 300 illustratively includes optical cavity component 302, light source component 304, and detector component 306, with the implantable product including at least optical cavity component 302, possibly in combination with one or more other components, as described below.

Optical cavity component 302 could be an implementation of implantable product 10 in FIG. 1 in a long, narrow structure resembling a short needle as described below in relation to exemplary implementations. A compact device with such a structure could be inserted in a minimally invasive manner under a human's skin to enable continuous detection of glucose without further invasive procedures.

In the illustrated example, optical cavity component 302 is shown in cross-sectional view, showing how light-reflective components 310 and 312 and a set of wall parts including wall 314 define containers 320 and 322 between light-reflective components 310 and 312. Each of containers 320 and 322 and bounding surfaces of components 310 and 312 can operate as a respective Fabry-Perot (FP) interferometer, for example, with the objective of obtaining values indicating concentration of glucose in surrounding fluid. For example, in some exemplary implementations described below, indices of refraction of small samples of surrounding interstitial fluid are measured, with each sample being contained within an FP optical cavity and the resulting output signal only being influenced by changes within the sample.

Such structures have been implemented in very small devices that are very sensitive. In some such implementations, wavelength of incident light from a laser is scanned to locate intensity peaks, such as of transmission modes. It might similarly be possible to increase specificity by probing or scanning in several discrete wavelength ranges.

Prototype devices including such structures have been successfully implemented that measure glucose changes with precision of 10% over the range 50 mg/dl to 500 mg/dl. In the visible spectral range, the refractive index increment of an aqueous glucose solution is about $1.38*10^{-6}$ per mg/dl, according to Weast, R. C., ed., *CRC Handbook of Chemistry and Physics*, $55^{th}$ Ed., Cleveland, Ohio: CRC Press, 1974, p. D-205. In order to achieve a sensitivity of 5 mg/dl it is therefore necessary to reliably measure refractive index changes of approximately $7*10^{-6}$, a change that translates to a wavelength shift of FP modes of about 5.5 pm. The FSR of FP modes, approximately 37 nm in the wavelength range 900-1100 nm for a mirror distance of 10 μm, can be tuned by an FP cavity's properties. A key value, for example, is distance between partially reflective mirrors bounding the FP cavity: A mirror distance of 430 μm results in an FSR of 790 pm at a probing wavelength around 950 nm, for example, so that glucose concentration changes of approximately 0 to 720 mg/dl can be detected by spectral shift of a single FP mode.

While glucose sensing could be implemented in almost any suitable wavelength range, it may be optimal to use a wavelength at which absorption and scattering of light by skin and tissue are minimized. This suggests that the range between 700-1200 nm is likely to be suitable, and a vertical-cavity surface-emitting laser (VCSEL) that emits at a wavelength in the 700-1200 nm range can be easily and precisely tuned to scan across an appropriate subrange such as across approximately 1.5 nm of wavelengths (approximately two modes) with current control, providing a suitable light source for illumination of optical cavities.

The cross section of FIG. 6 could be taken at a point along the length of the structure at which, when implanted under a human's skin, objects in interstitial fluid can transfer between the exterior and interior of each of glucose container 320 and non-glucose container 322 through respective filters described in more detail below. In each case, each container's respective filters are shown in its side wall disposed away from the other container, and could, for example, be mounted or otherwise attached to or connected in any suitable combination of one or more openings of any appropriate shape and size along the length of a container's side wall and/or in one or both of a container's end walls; these examples are merely illustrative, and filters could be mounted or otherwise attached to or connected in or through any appropriate part of the boundary of the container and in any appropriate way.

Container 320 is bounded by reflective surfaces of components 310 and 312 and also by a surface of wall 314; it can contain interstitial fluid filtered by filter 324. Container 322 is similarly bounded by other reflective surfaces of components 310 and 312 and also by the opposite surface of wall 314; it can contain interstitial fluid filtered by filters 326 and 328.

Each of filters 324 and 328 prevents a subset of objects that can affect optical characteristics from being transferred into containers 320 and 322 at a relatively rapid rate. In some successful implementations, filters 324 and 328 have been implemented as macromolecule or molecule weight cut-off (MWCO) filters that effectively prevent molecules over an appropriate size such as about 3 kDa or about 30 kDa from entering containers 320 and 322, respectively, and filters 324 and 328 could be implemented in various other ways. As a result of filters 324 and 326, transfer of objects such as large molecules, cells, and so forth occurs only at a relatively slow rate or possibly does not occur at all if filters 324 and 328 are highly effective.

Filter 326, on the other hand, prevents glucose from being transferred into container 322 at a relatively rapid rate, while allowing at least some other objects that pass through filter 328 to be transferred at a relatively rapid rate. In some successful implementations, filter 326 has been implemented as an ionophore membrane that only allows certain electrolytes, e.g. the ions of NaCl, to enter container 322, and therefore operates as a glucose-blocking filter. As a result, transfer of glucose into container 322 occurs only at a relatively slow rate or possibly does not occur at all if filter 326 is highly effective.

Due to the arrangement of filters described above, contents of containers 320 and 322 can be described as discussed above in relation to FIGS. 1-3, with the shared subset including electrolytes that affect optical characteristics and that pass through all of filters 324, 326, and 328 at a relatively rapid rate. The non-shared subset in container 320, on the other hand, includes glucose, which is predominantly in the non-shared subset. Container 322, in contrast, includes very few if any types of objects that are not also present in container 320. Therefore, non-glucose container 322 contains predominantly electrolytes; glucose container 320 contains electrolytes, glucose, and other objects below the maximum filter size; and neither of containers 320 and 322 contains large molecules or cells because they are transferred into the containers at zero or negligible rates.

In operation, optical cavity component 302 receives input light from light source component 304, which could include one or more tunable lasers such as VCSELs or other appropriate light sources as described above. In response, optical cavity component 302 operates as two parallel optical cavities, each of which provides output light to detector component 306, which has been successfully implemented with a separate photosensing detector for each cavity: One optical cavity includes container 320 and provides output light, represented by arrow 330, with information about index of refraction of contents of container 320; the other optical cavity includes container 322 and provides output light, represented by arrow 332, with information about index of refraction of contents of container 322. For example, if the optical cavities both operate as FP interferometers or as similar optical cavities with transmission or reflection modes, features of the modes of the two cavities will differ in a way that indicates difference of refractive index of contents of the respective containers. At the same time, the modes of the two cavities will be affected identically by some variations, such as in electrolyte concentration or in temperature, so that the difference between their modes will not be affected by such variations. As a result, non-glucose container 322 serves as a reference, with variation in glucose concentration being the predominant cause of difference between modes of the two cavities.

In response to output light from the optical cavities, the photosensing detectors in detector component 306 obtain sensing results that can include information about indices of refraction of contents of both containers, and the sensing results can be provided to an external component such as a CPU or other processor, as indicated by arrow 334. The CPU or other processor can use the sensing results to obtain information about glucose concentration, such as in one of the ways described below.

During operation in this manner, one or more of the illustrated components of system 300 could be controlled by a processor such as CPU 240 (FIG. 5). In a typical implementation, objects could be transferred into containers in component 302 by diffusion or, if pumping or the like were implemented, by being carried by flow of bodily fluid, but if power is available in the implantable product for other operations as described below, electrochemical or electromechanical transport processes could also be implemented to manipulate flow of bodily fluid, such as to assure representative sampling or to extend the operational life of the implantable product, and such processes could also be controlled by a processor. Power could be available in many possible ways, including, for example, by inductive coupling, from one or more batteries, or from one or more photocells or other electromagnetic receivers.

Figure 7:
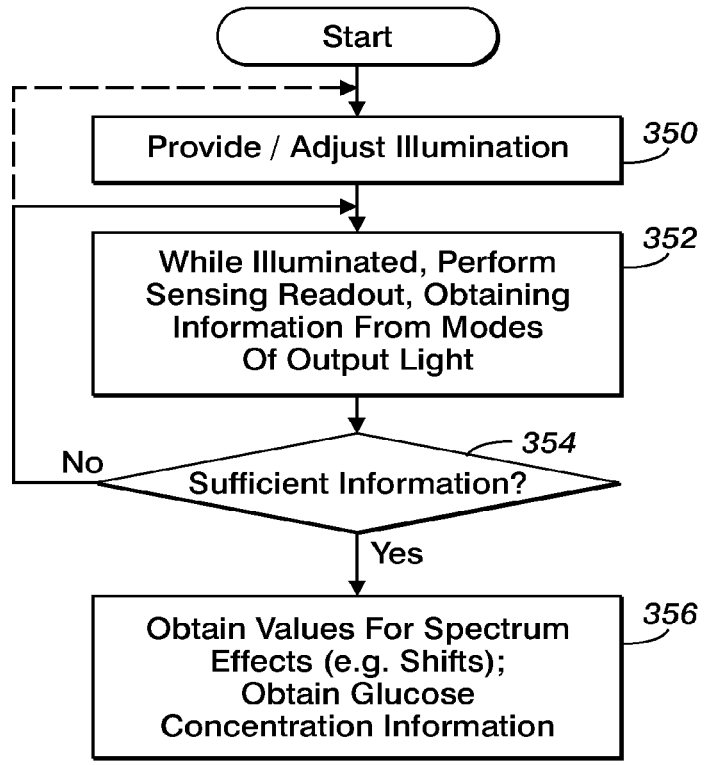
FIG. 7 is a flow chart showing operations of the analyte information routine in FIG. 5 as it could be implemented in a system as in FIG. 6.

FIG. 7 illustrates one example of how analyte information routine 274 (FIG. 5) could be implemented in a system like system 300 in FIG. 6. The routine in FIG. 7 follows a general strategy of varying illumination while iteratively performing a series of readout operations, each sampling output light intensity at an illuminating photon energy, until sufficient information is obtained, after which values for shifts or other spectrum effects of analyte and non-analyte objects can be obtained and used to obtain glucose concentration information. It would also be possible to obtain shift values several times, each after a subseries of iterations, and then combine or otherwise use a number of such shift values to obtain glucose concentration information.

The operation in box 350 begins by providing illumination, such as according to an appropriate waveform. In this operation, CPU 240 can determine the appropriate illumination, such as based on operator input, and can then provide signals to light source 304, such as through illumination control 250 (FIG. 5) to obtain the appropriate illumination. As noted above, a tunable VCSEL that emits at a wavelength in the 700-1200 nm range could be current-controlled to scan across an appropriate subrange of wavelengths such as across approximately 1.5 nm of wavelengths, with each iteration in FIG. 7 reading out photosensed quantities for a respective wavelength in the subrange, such as with rapid CCD readout, so that each complete scan involves as many iterations as necessary to adequately sample the subrange.

While illumination is provided, the operation in box 352 then performs sensing readout during an appropriate sensing period or series of sensing periods. In one exemplary approach, box 350 can continuously vary VCSEL laser wavelength across a subrange, such as with a sawtooth-like function that includes ramps separated by discontinuous inter-ramp transitions. Thousands of readout iterations can be performed during each ramp; with a ramp time of a millisecond, for example, readout could be performed more than once per microsecond.

The sensing results obtained from the sensing readout include information from the modes of the output light from both the glucose and non-glucose containers in optical cavity component 302; this information can be encoded, for example, in the ways described above, and particularly in a spectral characteristic or feature such as a shift of the respective spectral position of each of a set of peaks or valleys.

During the operation in box 352, CPU 240 may also provide signals to peripheral circuitry on an IC so that analog readout quantities are identified as resulting either from glucose container 320 or non-glucose container 322 and, if appropriate, adjusted. After adjustment, if any, analog quantities can be converted to digital signals for readout. The operation in box 352 can be implemented in whatever manner is appropriate for a given photosensing IC, whether a CCD or CMOS implementation, and regardless of whether readout is purely serial or is also parallel.

If information about analyte is encoded in intensity functions of one or more modes, this information can be included in sensing results in various ways. For example, an optical cavity could be iteratively illuminated at a series of wavelengths and intensity of its output light could be sensed with any appropriate photosensing device, even a single discrete photosensor, to obtain a time series of intensity-energy points that could be used to detect peak or valley shifts. For the sawtooth sampling technique described above, analog readout intensities from each ramp could be converted to digital values, and the digital values from each ramp could be processed with appropriate data processing operations to algorithmically obtain, e.g., a single digital value indicating time(s) within the ramp at which peak(s) occurred; peak time values could later be used in box 356 to obtain shift values. Any of a variety of algorithms could be employed, and it is foreseeable that improved peak detection algorithms will be developed in the future.

In a more complex implementation, detector component 306 can include a laterally varying transmission structure, so that each mode's reference and analog intensity-energy peaks (or valleys) have respective light (or dark) spots on a photosensing IC in detector component 306. Therefore, the sensing results can include information about one or both of position, size, and intensity of each light (or dark) spot and, accordingly, about the respective mode's intensity peaks (or valleys). If output light from each cavity includes intensity peaks (or valleys) for two or more modes, their respective light (or dark) spots could be tracked as described in co-pending U.S. Pat. No. 7,502,123 and incorporated herein by reference in its entirety.

The photosensed quantities read out in box 352 can also be digitally adjusted by CPU 240. In other words, suitable information can be obtained by CPU 240, such as from the digitized output or from other sources such as capacitive sensors of electrical conductance as described below; such information can then be used to adjust digitized values obtained for the glucose and non-glucose containers. For example, the operation in box 352 or a subsequent operation can make a data manipulation or adjustment to obtain "cavity-only absorption data", an expression that refers herein to values or other data in which information about absorption in an optical cavity is preserved while information is reduced about features exterior to the cavity such as inhomogeneities in illumination and external absorption, as described in co-pending U.S. Pat. No. 7,502,123 and incorporated herein by reference in its entirety. As will be understood, the encoding of absorption information in this manner allows removal of noise-like effects other than those from absorption coefficient inside the optical cavity, influences such as external perturbations, disturbances, or inhomogeneities. As a result, measurements of absorption can have a higher signal-to-noise ratio. Also, information can be recovered from encoded output light that is selectively sensitive to absorption changes inside the cavity.

If cavity-only absorption data, such as contrast values, are obtained both for the glucose and non-glucose containers, the value for glucose can be adjusted using the non-glucose container's values, such as by taking a difference; this is one example of "self-calibration" as that term is used herein. Self-calibration can be especially useful in removing noise-like effects that arise if light source 304 and/or detector 306 are spaced apart from optical cavity component 302, as would be the case for some of the implementations described below. Where input or output light must pass through bodily tissue and fluids, measurements of absorption are subject to noise, but self-calibration can produce a higher signal-to-noise ratio. As indicated above, self-calibration also reduces or eliminates effects of some variations, such as variations in electrolyte concentration and variations in temperature.

The operation in box 352 can also include other operations. For example, digital adjustment in box 352 can also include any necessary adjustments due to differences in sensing periods or other factors.

With the results from box 352, the operation in box 354 then branches based on whether sufficient information has been obtained in accordance with any appropriate criterion, such as a number of iterations or a minimum set of illuminations. If the criterion is not met, a further iteration is performed, beginning with box 352 as described above; alternatively, if illumination is adjusted for each iteration, the next iteration can begin by adjusting illumination in box 350. But if sufficient information has been obtained, CPU 240 can perform the operation in box 356 to obtain spectrum effect values such as shift values and to use them to obtain glucose concentration information, such as in the form of data for another routine or as output through external I/O 249. This operation can include algorithmically obtaining peak time values as described above, and can also include any additional adjustments, including adjustments based on electrical conductance, that were not performed in box 352. The operation in box 356 can also include further processing.

In one specific technique that has been successfully implemented with wavelength scanning as described above to obtain transmission mode output light, each iteration's analog signals are received, digitized and saved for the respective wavelength in an appropriate data structure for each container, in box 352. Then, in box 356, an operation is performed on the each container's data structure to identify wavelengths at which peak central energies occur. The identified wavelengths from the cavities can then be compared to obtain one or more displacement values indicating shift; for example, a first difference can be obtained between wavelengths of two containers.

Yet another possible implementation of box 352 could use a lock-in amplifier. Periodically varying incident wavelength could be provided by sinusoidally tuning the light source within the sampling wavelength subrange. Continuously photosensed transmission (reflection) intensities of two cavities could be fed into the lock-in amplifier, which on the one hand determines frequency of the intensity signals and on the other hand their phase shift relative to each other. This phase shift is another effect of spectrum-affecting (or spectrum-shifting) objects, and it indicates refractive index difference between the two cavities; therefore, it can be used in box 356 to obtain glucose concentration information.

In general, the operations in boxes 352 and 356 can, in combination, obtain values that indicate glucose concentration in surrounding interstitial fluid by any of a variety of suitable techniques, using both optical- and electrical-based information. For example, the values obtained can include refractive index values for each of containers 320 and 322 or differential values indicating difference in index of refraction between containers 320 and 322. As noted above, the difference in index of refraction between the two containers is attributable predominantly to changes in glucose concentration in interstitial fluid and eliminates not only effects of contaminants but also changes in index of refraction in the water solvent due to temperature change.

Operations in boxes 352 and 356 might be implemented to obtain values indicating glucose concentration by simply obtaining a differential value indicating wavelength or frequency shift between peak (or valley) positions or phase shift for FP transmission (or reflection) modes of containers 320 and 322. A differential value of this type could be obtained in any appropriate way, such as by comparing two analog values and then digitizing the resulting difference signal or by converting both values to digital values and then subtracting one from the other.

The operation in box 356 could alternatively be implemented in various other ways. For example, frequency, wavelength, or phase shift values could be used to obtain digital values that indicate refractive indices in containers 320 and 322, which could then be used to obtain glucose concentration.

In performing operations in boxes 352 and 356, CPU 240 can employ data structures (not shown) stored in memory 246 (FIG. 5). For example, photosensed intensity values from each iteration could be stored together with previously obtained information in a readout data structure. The operation in box 352 could update the readout data structure before completing each iteration, and then the readout data structure could be used in box 356 to obtain glucose concentration information. If, for example, the operation in box 356 obtains absorption values for glucose, another data structure could provide an absorption spectrum; similarly, refractive index dispersion could be obtained and provided.

The technique in FIG. 7 can also be combined with other types of measurements, such as Raman spectroscopy, intrinsic fluorescence spectroscopy and measurement of fluorescence lifetime, polarimetry to obtain rotation, and so forth, which could be performed using the same implantable product with additional operations similar to those described above; combining absorption spectrum measurement with orthogonal methods such as polarimetry can improve sensitivity and specificity. The operation in box 356 can be extended to perform multiple signal analysis.

Figure 8:
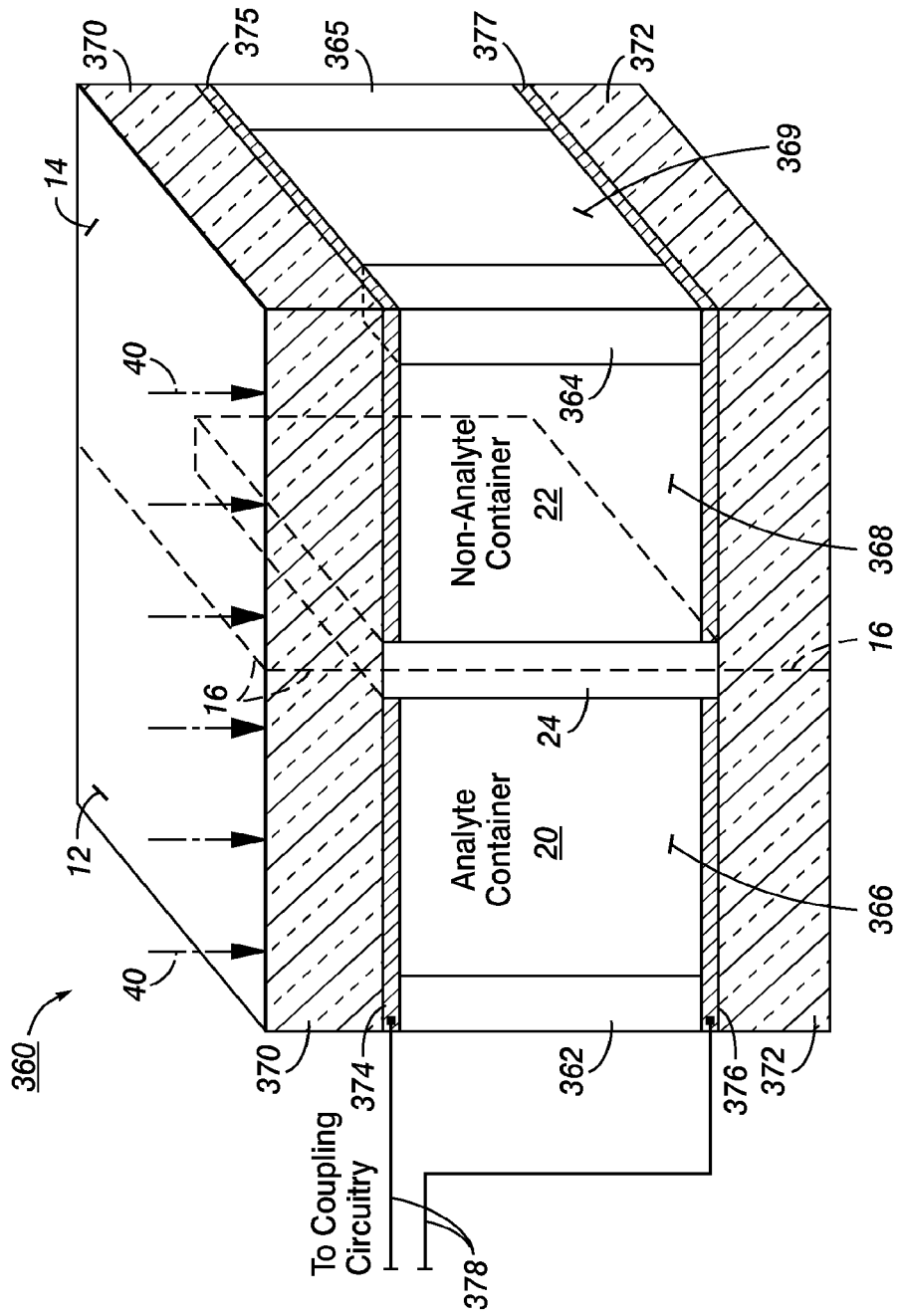
FIG. 8 is a perspective view of a component that is an implementation of an article as in FIG. 1.

FIG. 8 illustrates features of optical cavity component 360, another implementation of product 10 (FIG. 1) with similar parts labeled with the same reference numerals as in FIG. 1. If suitably implemented, optical cavity component 360 could be used in system 300 (FIG. 6) in place of optical cavity component 302. Component 360 is illustratively rectangular, with each part's entry and exit surfaces being approximately square for easier illumination; and FIG. 8 shows one side of component 360.

As in FIG. 1, part 12 includes analyte container 20 and part 14 includes non-analyte container 22. Each container can have an unattached side away from the other container, an attached side toward the other container, and lateral surface between the unattached and attached sides. Wall 24 is at the attached sides of both containers. The lateral surfaces of container 20 and 22 extends leftward and rightward, respectively, from wall 24, with the illustrated front side extending to posts 362 and 364, respectively. Between wall 24 and posts 362 and 364, the front sides are covered by filter assemblies 366 and 368, respectively; assembly 366 could include a filter like filter 324 (FIG. 6), while assembly 368 could include filters like filters 326 and 328 (FIG. 6); the rear sides of containers 20 and 22 could have similar filter assemblies (not shown) extending to similar posts, with post 365 at the rear of container 22 being shown in the illustrated view. Opposite wall 24, the unattached side of container 20 is similarly covered by another filter assembly (not shown) that extends from post 362 backward to its rear post (not shown) and could include a filter like filter 324. The unattached side of container 22, as shown, is similarly covered by filter assembly 369, extending between posts 364 and 365, which could include filters like filters 326 and 328. In general, objects in interstitial fluid or other bodily fluid can continuously diffuse through the filter assemblies whenever concentration gradient occurs, allowing for continuous monitoring or other sensing operations. Rate of diffusion into containers 20 and 22 is increased by covering not only their front and rear lateral sides but also their unattached sides with filter assemblies, thus increasing area of bounding regions through which objects in bodily fluid can be transferred into each container through its filter assemblies.

As in FIG. 1, parts 12 and 14 each receive input light as indicated by arrows 40, illustratively through a light interface surface of structure 370. Parts 12 and 14 can provide transmitted output light through an opposite light interface surface of structure 372 and can provide reflected output light (not shown) back through the same light interface surface of structure 370.

Structures 370 and 372 can each be implemented with glass or other light-transmissive material. Each of structures 370 and 372 can also include or support respective light-reflective components disposed toward each other for optical cavity operations. Electrodes 374 and 375, supported on opposite sides of container 20 by structures 370 and 372 respectively, can also operate as the light-reflective components, such as metallic mirrors, or can be light-transmissive conductors, in which case structures 370 and 372 include other light-reflective components such as mirrors. Similarly, electrodes 376 and 377, supported on opposite sides of container 22 by structures 370 and 372 respectively, can operate as light-reflective components, such as metallic mirrors, or can be light-transmissive conductors, with structures 370 and 372 including other light-reflective components such as mirrors. Note that electrodes 374, 375, 376, and 377 would not be needed for techniques described below if patterned light-reflective components included in structures 370 and 372 can also operate as electrodes; such light-reflective components could take the place of electrodes 374, 375, 376, and 377.

Lines 378 connected to electrodes 374 and 375 are also connected to coupling circuitry (not shown) through which signals from electrodes 374 and 375 can be provided to external circuitry (not shown), such as through inductive coupling or other appropriate coupling techniques. Electrodes 374 and 375, lines 378, and the coupling circuitry therefore make it possible to measure fluid electrical conductance across contents of analyte container 20.

To a first approximation, fluid electrical conductance in container 20 is directly proportional to electrolyte concentration in the container. Therefore, fluid electrical conductance can be used, as in boxes 352 and 356 in FIG. 7, to determine level of hydration, which can then be used to derive a value for glucose from shift values or other values indicating spectrum effects; measured fluid conductance of analyte can be used to adjust sensing results to eliminate effects of interfering objects on optical-based measurements of analyte characteristics such as refractive index. Although DC methods could be used to measure fluid electrical conductance across electrodes as in component 360, AC conductance can be measured by capacitive methods and may therefore be more suitable for use in an implanted product because electrodes employed in DC methods could become contaminated. Although FIG. 8 shows electrodes and lines for analyte conductance measurement, component 360 does not include a reference cavity, and such measurement is expected to be especially useful in implementations with reference cavities, several examples of which are described below.

Component 360 in FIG. 8 also illustrates a typical rectangular shape for an article like product 10 as in FIG. 1. Insertion into a human body should be achievable with transverse outer dimensions approximating 2.0 mm, and dimensions approximating 1.0 mm would make insertion easier. Current thin film fabrication technology can easily produce a structure of this size.

Openings into each container in component 360 can be shaped, sized, and located for the required update time constant and other constraints of the application; for example, for monitoring a homogeneous fluid for glucose, it may be desirable for objects to diffuse into each container at the greatest feasible volume. Since diffusion rate is proportional to area for a given filter structure, and since diffusion time affects accuracy of measurements, an objective is to maximize diffusion through the filter assemblies, such as by increasing their area so that they cover as much of the boundaries of analyte and non-analyte containers as possible. In the illustrated implementation, this is promoted by providing filter-covered openings on all sides except the sides where light-reflective components bound optical cavities, i.e. in structures 370 and 372; if each of parts 12 and 14 is shaped as a cube, approximately 100% of its unattached side plus approximately 50% of the lateral surface between its attached and unattached sides would be object transfer regions, so that the total area of its object transfer regions might be equal to approximately 75% of the area of its lateral surface, e.g. a few percent less than 75%.

It might be possible to increase object transfer regions above 75% of the area of lateral surfaces by structuring component 360 so that each optical cavity's light-reflective surfaces are its unattached and attached sides, i.e. its left and right sides in the view in FIG. 8; in this case, nearly all of the lateral surface area would be available for object transfer regions, subject only to structural constraints, so that a cube-like container's object transfer regions might have an area exceeding 75% of the area of its lateral surface, conceivably approaching 90% or even 95% of the area of its lateral surface. In operation, transmission mode output light from one cavity illuminates the other cavity whose transmission mode output light is photosensed to obtain information about both cavities. Techniques such as this, in which cavities are in effect illuminated in series rather than in parallel, might, however, require more sophisticated data processing operations to obtain shift values and glucose concentration, as in box 356 in FIG. 7.

Component 360 could be implemented with a wide variety of types of optical cavity techniques. Component 360 could also be implemented with a tunable cavity, such as with deformable spacers, to set its wavelength range during manufacture or to adjust it during use, to provide a different set of sample points at each position. In any case, component 360 could be used in a system that applies referencing techniques to reduce the effects of noise and inhomogeneities, possibly including self-calibration and other types of referencing as mentioned herein, including techniques appropriate to tuning a laser across at least one FSR of a cavity's spectrum.

Figure 9:
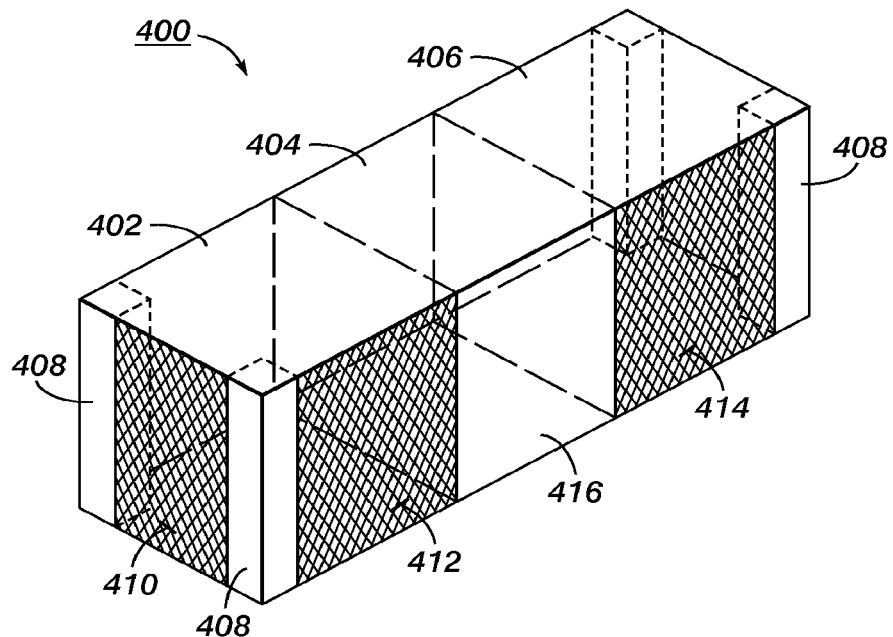
FIG. 9 is a top plan view of another component that is an implementation similar to the optical cavity structure in FIG. 4.

FIG. 9 illustrates features of optical cavity component 400, another implementation similar to structure 202 (FIG. 4) with an additional reference container, such as containing a reference fluid (e.g. water, another liquid, or gas), a reference solid, or vacuum with a well-defined refractive index. If suitably implemented, optical cavity component 400 could similarly be used in system 300 (FIG. 6) in place of optical cavity component 302. Like component 360 (FIG. 8), component 400 is rectangular, and FIG. 9 shows a perspective view, showing three containers separated by wall-like parts represented by dashed lines, analyte container 402, reference container 404, and non-analyte container 406.

Analyte container 402 and non-analyte container 406 each have posts 408 at the corners on their unattached sides disposed away from each other and their attached sides both connect to container 404. Filter assembly 410 is attached between posts 408 on the unattached side of container 402, and a similar filter assembly (not shown) would be on the oppositely disposed unattached side of container 406. Filter assemblies 412 and 414 are similarly attached on the rightward lateral sides of containers 402 and 406, and similar filter assemblies (not shown) could be on their opposite, leftward lateral sides. Through diffusion through the filter assemblies at their sides, containers 402 and 406 can receive objects from interstitial fluid when concentration gradients arise. In contrast, reference container 404 is closed at rightward end 416 and also at its leftward end, and holds a reference fluid (e.g. water), solid, or vacuum. In other respects, component 400 can be implemented similarly to component 360 (FIG. 8).

In the illustrated example, the filter assemblies on the sides of analyte container 402 can be implemented with a filter similar to filter 324 (FIG. 6). Similarly, the filter assemblies on the sides of non-analyte container 406 can be implemented with filters similar to filters 326 and 328 (FIG. 6). Since diffusion rate is proportional to area for a given filter structure, and since diffusion time affects accuracy of measurements, an objective here again is to maximize diffusion through the filter assemblies, such as by increasing their area to cover as much of the boundaries of analyte and non-analyte containers as possible, as described above in relation to FIG. 8.

Figure 10:
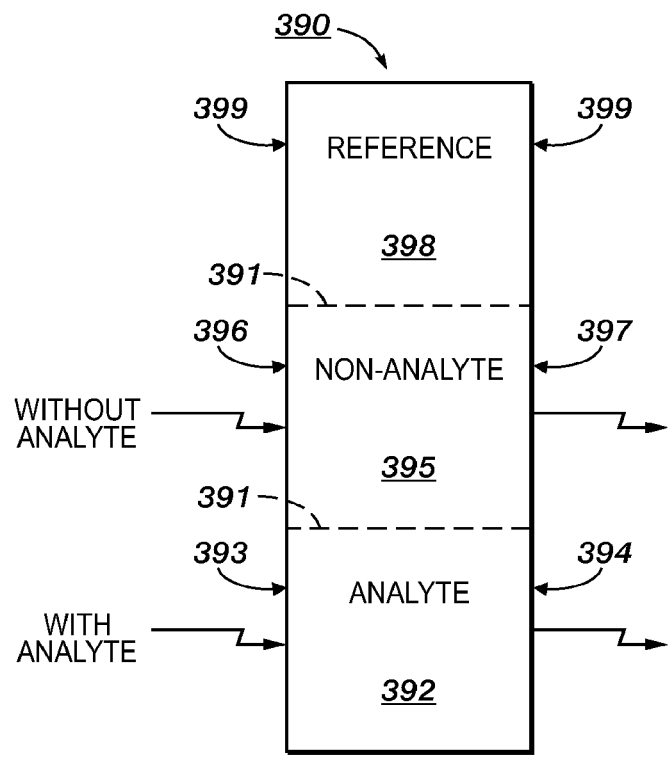
FIG. 10 is a top plan view of another component that is an implementation of an article similar to that in FIG. 9.

FIG. 10 illustrates features of optical cavity component 390, another implementation similar to component 400 (FIG. 9) but with containers in a different order that is more suitable to flow than to diffusion. If suitably implemented, optical cavity component 390 could be used in system 300 (FIG. 6) in place of optical cavity component 302. Like component 400 (FIG. 9), component 390 is illustratively rectangular, divided into three containers by wall-like parts represented by dashed lines 391 and with each container labeled with a description of possible contents when component 390 is operated in interstitial fluid that includes water, sodium chloride, glucose, and other types of objects such as lactic acid and so forth. To provide flow, the analyte and non-analyte containers could each have at least one channel end covered by a structure that performs a fluidic operation similar to pumping in order to draw filtered bodily fluid into the container through respective filter assemblies. In general, interstitial fluid or other bodily fluid can be continuously drawn through filter assemblies and through the containers to allow for continuous monitoring or other sensing operations.

Analyte container 392 can receive surrounding interstitial fluid through a filter assembly at its inlet end 393, and the interstitial fluid can be pumped by a pump device (not shown) at its outlet end 394. Similarly, non-analyte container 395 can receive surrounding interstitial fluid through a filter assembly at its inlet end 396, and the interstitial fluid can be pumped by a pump device (not shown) at its outlet end 397. Each of containers 392 and 395 can operate as a tube-like fluidic channel extending between opposite ends at lateral sides of component 390. In contrast, reference container 398 is closed at both its ends 399, and holds a reference fluid (e.g. water), solid, or vacuum. In other respects, component 390 can be implemented similarly to component 400 (FIG. 9).

In the illustrated example, the filter assembly at inlet end 393 of analyte container 392 can be implemented with a filter similar to filter 324 (FIG. 6). Analyte container 392 illustratively contains not only water from the interstitial fluid, but also all objects in the interstitial fluid that are less than an appropriate maximum size greater than glucose molecules; such objects include sodium chloride, glucose, and various other objects, such as lactic acid and many others.

The filter assembly at inlet end 396 of non-analyte container 395, on the other hand, can be implemented with filters similar to filters 326 and 328 (FIG. 6). Non-analyte container 395 illustratively contains only water and sodium chloride from the interstitial fluid.

Component 390 (FIG. 10) makes it possible to make absolute measurements of refractive indices of contents of containers 392 and 395 by reference to that of contents of container 398. Similarly, component 400 (FIG. 9) makes it possible to make absolute measurements of refractive indices of contents of containers 402 and 406 by reference to that of contents of container 404. In other words, containers 398 and 404 serve as absolute references.

It appears possible that only the glucose concentration in interstitial fluid is independent of hydration level, while concentrations of all other types of spectrum-affecting or spectrum-shifting objects change with hydration level but maintain constant ratios with respect to each other despite effects such as dehydration or hyponatremia. Therefore, a single value, $n_{AllLow}$, can represent the contribution to refractive index of all non-glucose objects in containers 392 and 402; if a value for $n_{AllLow}$ is obtained, it can be used with the absolutely measured refractive index $n_{Total}$ of containers 392 and 402 to obtain $n_{glucose}=n_{Total}-n_{AllLow}$, and $n_{glucose}$ can then be used to obtain glucose concentration.

Further, the non-glucose refractive index $n_{AllLow}$ can be approximated as proportional to the refractive index of one non-glucose type of objects, such as sodium chloride. Under this approach, one begins by obtaining the refractive index $n_{NaCl}$ for sodium chloride in interstitial fluid (which implicitly indicated hydration level, include results of conditions such as dehydration and hyponatremia) and a concentration coefficient $C_c$ that indicates the ratio of $n_{AllLow}$ to $n_{NaCl}$, a ratio that should be approximately constant over hydration level, which varies over time. The coefficient $C_c$ can be determined, for example, by initially measuring blood plasma values to obtain an initial value and then subsequently adjusting the initial value by comparing measured glucose values with blood glucose values during times of stable glucose concentration, in effect calibrating $C_c$. Once $C_c$ has been calibrated in this manner or has been obtained in some other way and the absolutely measured refractive index $n_{NaCl}$ of containers 395 and 406 has been obtained, $n_{AllLow}$ can be obtained using the relationship $n_{AllLow}=C_c*n_{NaCl}$.

This technique can be combined with techniques described above in relation to FIG. 7. For example, operations can be performed in box 356 (FIG. 7) to identify wavelengths at which peak central energies occur in each of the three containers in FIG. 9. A first difference value can be obtained indicating the difference in wavelength between the peak central energies of non-analyte container 406 and reference container 404; this first difference value can then be multiplied by a constant $C_c$ as described above to obtain an adjusted wavelength, and a second difference value can be obtained indicating the difference between the adjusted wavelength and the identified wavelength of analyte container 402, which indicates glucose concentration.

Object transfer control techniques based on selective filtering, such as of sodium chloride, may be advantageous because polarized molecules can often be very effectively selected, while it may be difficult to make a sharp distinction between objects with weights above and below some maximum. To the extent that recalibration might be required, it could be done, e.g. by making a conventional glucose concentration measurement periodically, such as once a week.

FIGS. 11-18 illustrate features of several other exemplary implementations of system 300 (FIG. 6). In general, however, system 300 could be implemented in many different ways, and can include various implantable products that include optical cavity structures of various kinds; various types of filters, membranes, and other fluidic components; various combinations of containers with and without absolute reference containers; various types and combinations of light sources; and various types of detectors in addition to the examples described below.

Figure 11:
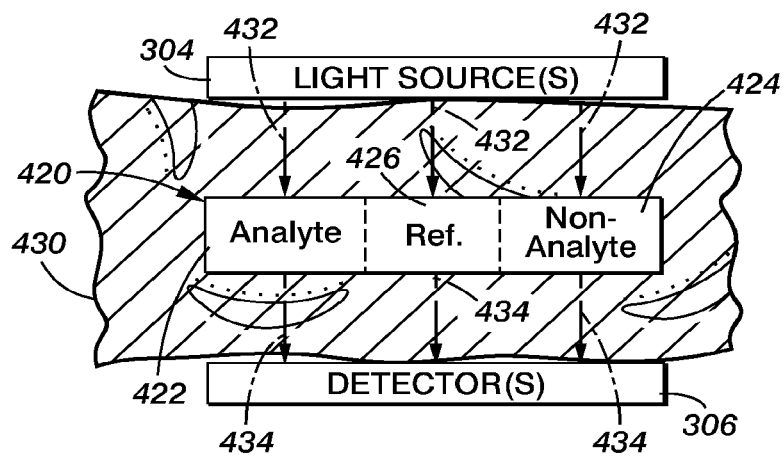
FIG. 11 is a schematic diagram of an implementation of a system with a component similar to that in FIG. 9.

FIG. 11 illustrates a configuration in which implantable product 420 includes neither light source component 304 nor detector component 306, but does include analyte container 422, non-analyte container 424, and reference container 426. As shown, product 420 has been implanted in body part 430, which could be human dermis, and can be illuminated by light source component 304 on or near an exterior surface of body part 430, providing input light represented by arrows 432. In response to appropriate illumination, respective optical cavities that include containers 422, 424, and 426 operate to provide output light represented by arrows 434. Detector component 306, also on or near an exterior surface of body part 430, photosenses the output light, providing sensing results as described above.

The configuration in FIG. 11 may be especially appropriate if input and output light are in the wavelength range 600-1100 nm, in which absorption by water and tissue allows a transmission window in which it may be possible to measure absorption of certain important analytes such as glucose. If implemented as a completely passive optical unit, product 420 may not require any electrical power. The configuration in FIG. 11 may, however, involve issues of orientation of components to ensure that illumination and detection are efficiently performed.

Orientation of components can result in non-perpendicular incidence of input light on optical cavities. Unless all output light is incident on one position of the detector component or the detector component has only a single large area as with some PSDs, adjustments can be made to correct for non-perpendicular incidence of input light: For example, if the light source component emits light from a point source at many different angles that are accordingly transmitted through the cavities at various angles, the detector component's photosensitive surface receives the output light at many different angles, but each cell of a photosensor array would receive only a very small angular distribution; therefore, if the angle could be known, as would be the case in a fixed geometry but may not be the case in FIG. 11, the angle-induced variation can be easily corrected. Furthermore, angle-induced variations can be corrected by detecting two transmission maxima (or reflection minima) in one cavity. Their spacing is the free spectral range of the cavity which is proportionally affected by variations in the incident light angle. Therefore, by determining the free spectral range, variations in the incident light angle may be compensated for by, for example, dividing the maximum's (minimum's) position by the free spectral range.

Figure 12:
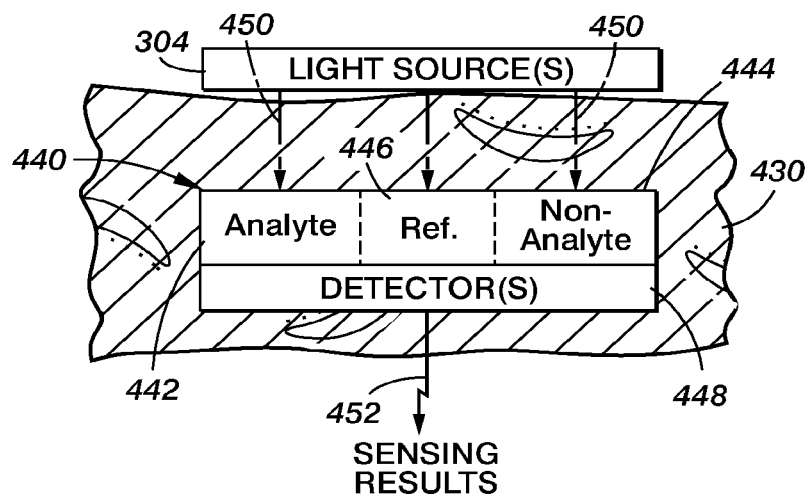
FIG. 12 is a schematic diagram of another implementation of a system similar to that in FIG. 9.

FIG. 12 illustrates a configuration in which implantable product 440 does not include light source component 304, but does include analyte container 442, non-analyte container 444, reference container 446, and detector component 448. As shown, product 440 has again been implanted in body part 430, and, as in FIG. 11, can be illuminated by light source component 304 on or near an exterior surface of body part 430, providing input light represented by arrows 450. In response to appropriate illumination, respective optical cavities that include containers 442, 444, and 446 operate to provide output light to detector component 448, connected to containers 442, 444, and 446 in any appropriate way. Detector component 448 photosenses the output light and provides sensing results, such as by transmitting electromagnetic or other signals represented by arrow 452.

The configuration in FIG. 12 may also be appropriate if input and output light are in the wavelength range 600-1100 nm, for the same reasons as FIG. 11. In this configuration, product 440 must have an electrical power source for detector component 448. It may also involve issues of orientation of components to ensure that illumination is efficiently performed. If the measurements are referenced to a reference medium many of the issues with regard to the misalignment of the components can be corrected, since analyte and reference measurement are affected in the same manner.

Figure 13:
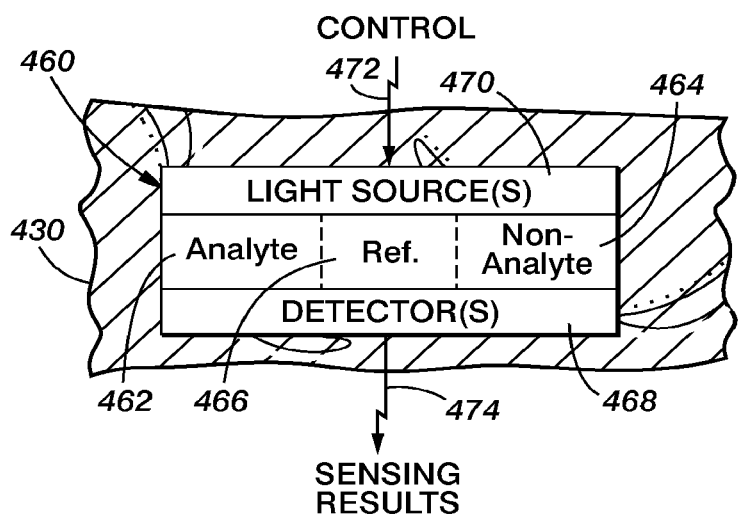
FIG. 13 is a schematic diagram of yet another implementation of a system with a component similar to that in FIG. 9.

FIG. 13 illustrates a configuration in which implantable product 460 includes analyte container 462, non-analyte container 464, reference container 466, detector component 468, and light source component 470. As shown, product 460 has again been implanted in body part 430, but does not require illumination from outside the body as in FIGS. 11 and 12. Instead, light source component 470, connected to containers 462, 464, and 466 in any appropriate way, can illuminate the optical cavities that include containers 462, 464, and 466 in response to receiving electromagnetic or other control signals represented by arrow 472. In response to appropriate illumination, the optical cavities that include containers 462, 464, and 466 operate to provide output light to detector component 468, connected to containers 462, 464, and 466 in any appropriate way. As in FIG. 12, detector component 468 photosenses the output light and provides sensing results, such as by transmitting electromagnetic or other signals represented by arrow 474.

The configuration in FIG. 13 may be appropriate not only if input and output light are in the wavelength range 600-1100 as in FIGS. 11 and 12, but also in the range 2.1-2.5 µm, because absorption by water and tissue is greatly reduced or eliminated. The configuration in FIG. 13 similarly must have an electrical power source for both light source component 470 and detector component 468. It may also involve issues of orientation of components to ensure that illumination is efficiently performed, although these issues are greatly reduced in this case since all components can be fixed relative to each other.

Figure 14:
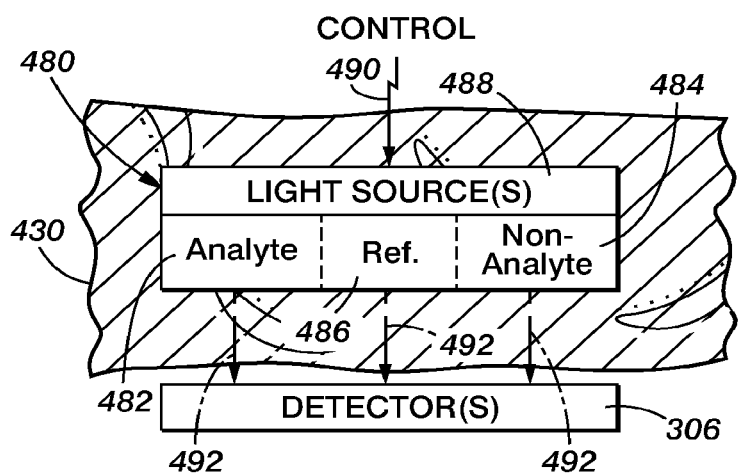
FIG. 14 is a schematic diagram of yet another implementation of a system with a component similar to that in FIG. 9.

FIG. 14 illustrates a configuration in which implantable product 480 includes analyte container 482, non-analyte container 484, reference container 486, and light source component 488, while detector component 306 is separate, as in FIG. 11. As shown, product 480 has again been implanted in body part 430, but does not require illumination from outside the body as in FIGS. 11 and 12. Instead, light source component 488, connected to containers 482, 484, and 486 in any appropriate way, can illuminate the optical cavities that include containers 482, 484, and 486 in response to receiving electromagnetic or other control signals represented by arrow 490. In response to appropriate illumination, the optical cavities that include containers 482, 484, and 486 operate to provide output light, represented by arrows 492. Detector component 306, again on or near an exterior surface of body part 430, photosenses the output light, providing sensing results as described above.

The configuration in FIG. 14 similarly must have an electrical power source for light source component 488. It can also involve other issues mentioned above in relation to FIGS. 11-13.

FIGS. 15-18 illustrate approaches in which an implantable product includes neither light source nor detector, but in which reflection is used so that light source and detector components can be on the same side of a body part, in some cases included in a single unit. The exemplary implementation of FIG. 15 reflects output light in a transmission mode, while those of FIGS. 16-18 use reflection modes. It would also, of course, be possible to combine both reflection techniques, using both transmission and reflection modes. Issues mentioned above in relation to FIGS. 11-14 are also relevant to FIGS. 15-18.

Figure 15:
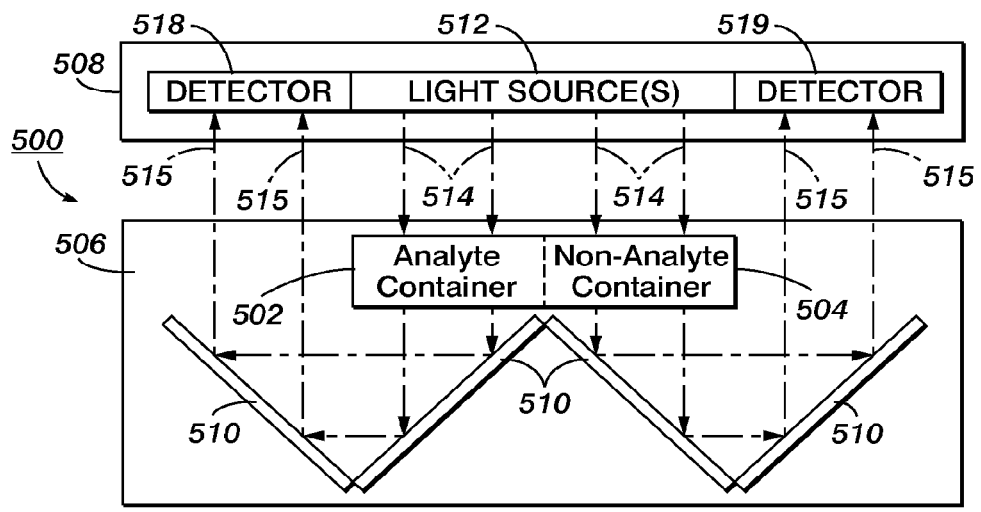
FIG. 15 is a schematic diagram of another implementation of a system with a component similar to that in FIG. 6, but with a reflection component.

FIG. 15 illustrates a configuration in which implantable product 500, which could be a passive device, includes analyte container 502, non-analyte container 504, and reflection component 506, while light source/detector unit 508 is separate. Product 500 has again been implanted in a body part, with reflection component 506 positioned away from an exterior surface of the body part on or near which unit 508 is positioned in use, possibly by being attached to skin. Reflection component 506 includes a retroreflector or similar combination of optical components that, as represented by mirrors 510, direct output light back in the direction from which input light is received from unit 508.

Unit 508 includes light source 512, which could, for example, be an array of lasers, a single laser with a beam splitter, or another suitable light source; in operation, light source 512 provides input light, represented by arrows 514. In response to appropriate illumination, respective optical cavities that include containers 502 and 504 operate to provide output light represented by arrows 515 and 516, respectively. Output light is reflected within reflection component 506, such as by mirrors 510, and emerges from the exterior surface of body part 410 where unit 508 is positioned.

Unit 508 also includes detectors 518 and 519, configured relative to light source 512 so that they receive the output light represented by arrows 515 and 516, respectively. Detector 518 therefore provides sensing results that include information about refractive index of contents of analyte container 502, while detector 519 provides sensing results that include information about refractive index of contents of non-analyte container 504. The sensing results from detectors 518 and 519 can be received by additional circuitry (not shown) in unit 508 or can be received from unit 508 by external circuitry (not shown), and the additional or external circuitry can perform operations, such as described above in relation to boxes 352 and 356 (FIG. 7), to obtain analyte information such as presence or concentration of an analyte.

FIG. 15 could also be used with other versions of unit 508. For example, one or both of detectors 518 and 519 could be interchanged with their light sources, so that one or both sides of product 500 could be illuminated and provide its output light in the opposite direction.

An implementation as in FIG. 15 could be advantageous if it eliminates the need to deliver power to an implanted device while allowing a small-sized implantable device comparable to that illustrated in FIG. 11; for example, with optical cavity mirror reflectivity in a range between approximately 50-70%, cavity thickness in a range between approximately 300-600 µm and lateral dimensions such as 3 mm×1 mm would be appropriate. With currently available techniques, however, an implementation as in FIG. 15 is likely to be larger in size than an active device as in FIG. 12, which, however, requires power for detector 448. An implementation as in FIG. 15 could advantageously be designed to minimize light passage through tissue and as a self-contained module, such as of glass. It could also be extended to one or more additional containers with respective mirrors, such as above and below the plane of containers 502 and 504.

Figure 16:
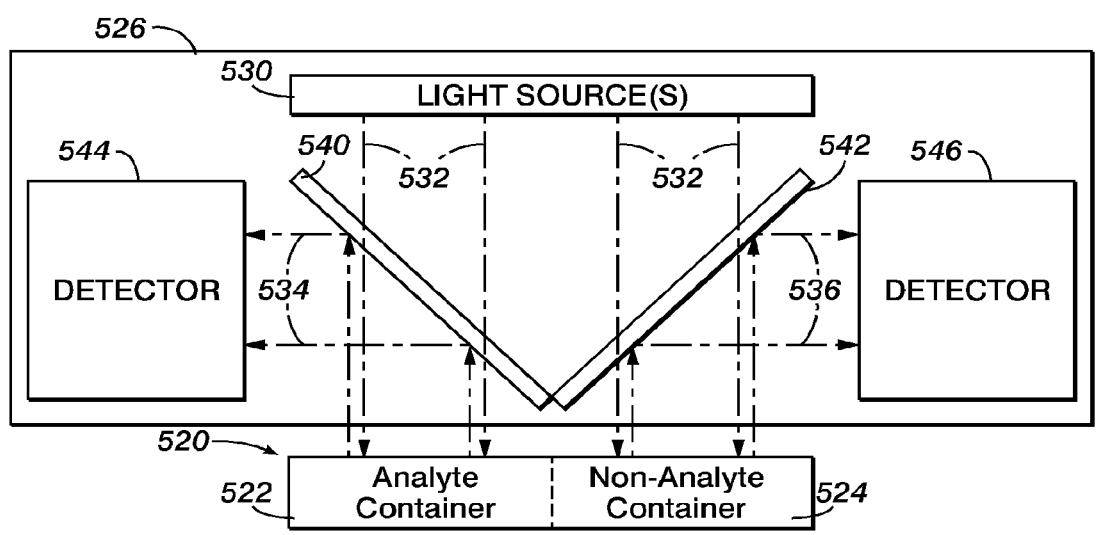
FIG. 16 is a schematic diagram of another implementation of a system similar to that in FIG. 6, but sensing reflection modes.
Figure 17:
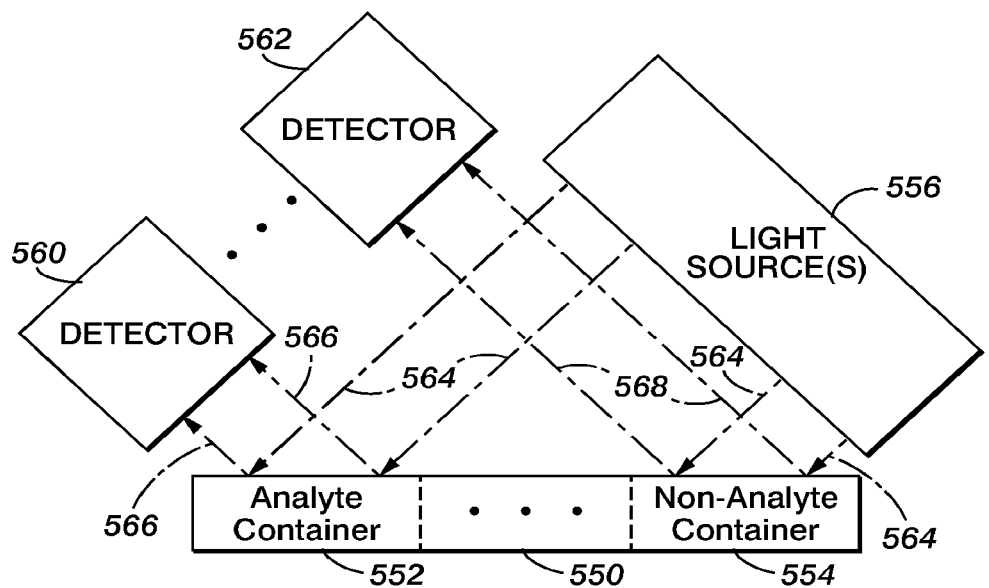
FIG. 17 is a schematic diagram of an implementation of a system similar to that in FIG. 4, also sensing reflection modes.
Figure 18:
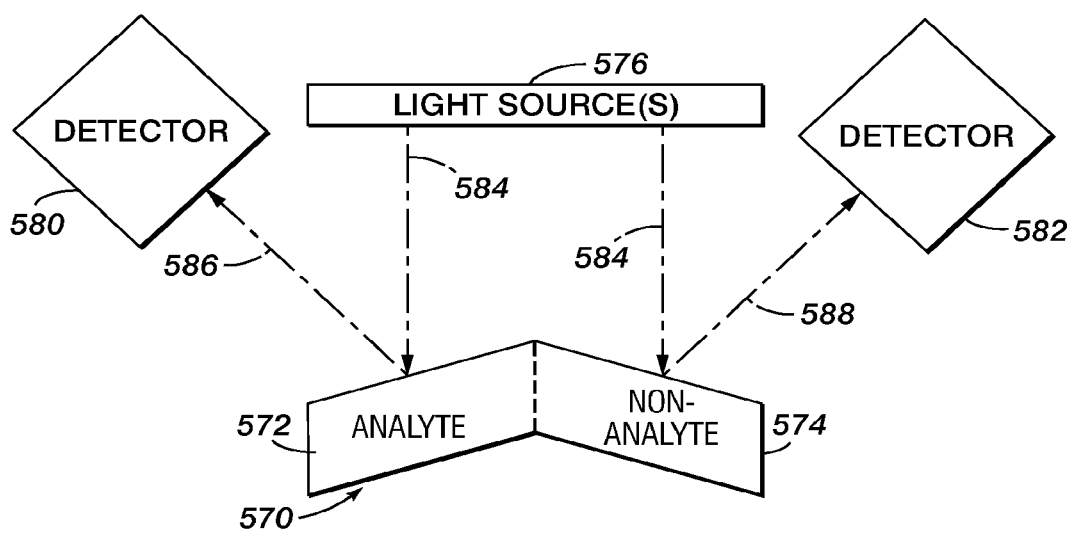
FIG. 18 is a schematic diagram of components in yet another implementation of a system similar to that in FIG. 6, also sensing reflection modes.

The configurations illustrated schematically in FIGS. 16-18 share some possible advantages of the configuration in FIG. 15 and also do not inherently require reflection component 506 so that they might allow a small-sized implantable device as in FIG. 11. In each case, appropriate measures are taken so that reflection mode output light can be detected at a position different than light source position.

FIG. 16 illustrates a configuration in which implantable product 520, which could be implemented as described above in relation to FIG. 11, includes analyte container 522 and non-analyte container 524, while light source/detector unit 526 is separate. As above, product 520 can be implanted in a body part (not shown), and unit 526 can be positioned on or near an exterior surface of the body part, possibly by being attached to skin.

Unit 526 includes light source 530, which could, for example, be an array of lasers, a single laser with a beam splitter, or another suitable light source; in operation, light source 530 provides input light, represented by arrows 532. In response to appropriate illumination, respective optical cavities that include containers 522 and 524 operate to provide output light represented by arrows 534 and 536, respectively. Output light emerges from the exterior surface of the body part where unit 526 is positioned.

Unit 526 also includes beam splitters 540 and 542 which reflect output light represented by arrows 534 and 536 toward detectors 544 and 546, respectively. Detector 544 therefore provides sensing results that include information about refractive index of contents of analyte container 522, while detector 546 provides sensing results that include information about refractive index of contents of non-analyte container 524. The sensing results from detectors 544 and 546 can be handled, for example, as described above in relation to FIG. 15.

Like FIG. 16, the technique of FIG. 17 could be extended to include one or more It could also be extended to one or more additional containers, such as above and below the plane of containers 522 and 524. In this modification, unit 526 could also include additional mirrors and detectors positioned and oriented appropriately to receive output light from the additional containers.

FIG. 17 illustrates a configuration in which implantable product 550, which could similarly be implemented as described above in relation to FIG. 11, includes analyte container 552 and non-analyte container 554 and could optionally include one or more reference containers or other appropriate containers between them as suggested by ellipses. As above, product 550 can be implanted in a body part (not shown), and light source 556 and detectors 560 and 562 can be positioned on or near an exterior surface of the body part, possibly by being attached to skin and possibly being in a unit as described above in relation to FIGS. 15 and 16.

Light source 556, which could, for example, be an array of lasers, a single laser with a beam splitter, or another suitable light source, provides input light, represented by arrows 564 which are illustratively oblique rather than normal to the entry surface of optical cavities in product 550. In response to appropriate illumination, respective optical cavities that include containers 552 and 554 operate to provide output light represented by arrows 566 and 568, respectively, also oblique rather than normal to the exit surface. Because of obliqueness as illustrated, beam splitters as in FIG. 16 are unnecessary.

Output light emerges from the exterior surface of the body part, with output light represented by arrows 566 and 568 being received by detectors 560 and 562, respectively. Detector 560 therefore provides sensing results that include information about refractive index of contents of analyte container 552, while detector 562 provides sensing results that include information about refractive index of contents of non-analyte container 554. The sensing results from detectors 560 and 562 can also be handled, for example, as described above in relation to FIG. 15.

FIG. 18 illustrates a configuration in which implantable product 570 includes analyte container 572 and non-analyte container 574. Unlike other exemplary implementations described above, containers 572 and 574 have entry and exit surfaces that are not aligned but rather form an oblique angle with a vertex where they meet. As above, product 570 can be implanted in a body part (not shown) with the vertex disposed toward an exterior surface of the body part, and light source 576 and detectors 580 and 582 can be positioned on or near the exterior surface of the body part toward which the vertex is disposed, possibly attached to skin or in a unit as described above in relation to FIGS. 15 and 16.

Light source 576, which could, for example, be an array of lasers, a single laser with a beam splitter, or another suitable light source, provides input light, represented by arrows 584 which can be normal to the body part's exterior surface but, as a result of positioning of product 570, oblique to entry surfaces of optical cavities in product 570. In response to appropriate illumination, respective optical cavities that include containers 580 and 582 operate to provide output light represented by arrows 586 and 588, respectively, which are oblique rather than normal to the optical cavity exit surfaces and also to the body part's exterior surface. Because of obliqueness as illustrated, beam splitters as in FIG. 16 are again unnecessary, as in FIG. 17.

Output light emerges from the exterior surface of the body part, with output light represented by arrows 586 and 588 being received by detectors 580 and 582, respectively. Detector 580 therefore provides sensing results that include information about refractive index of contents of analyte container 572, while detector 582 provides sensing results that include information about refractive index of contents of non-analyte container 574. The sensing results from detectors 580 and 582 can also be handled, for example, as described above in relation to FIG. 15.

Figure 19:
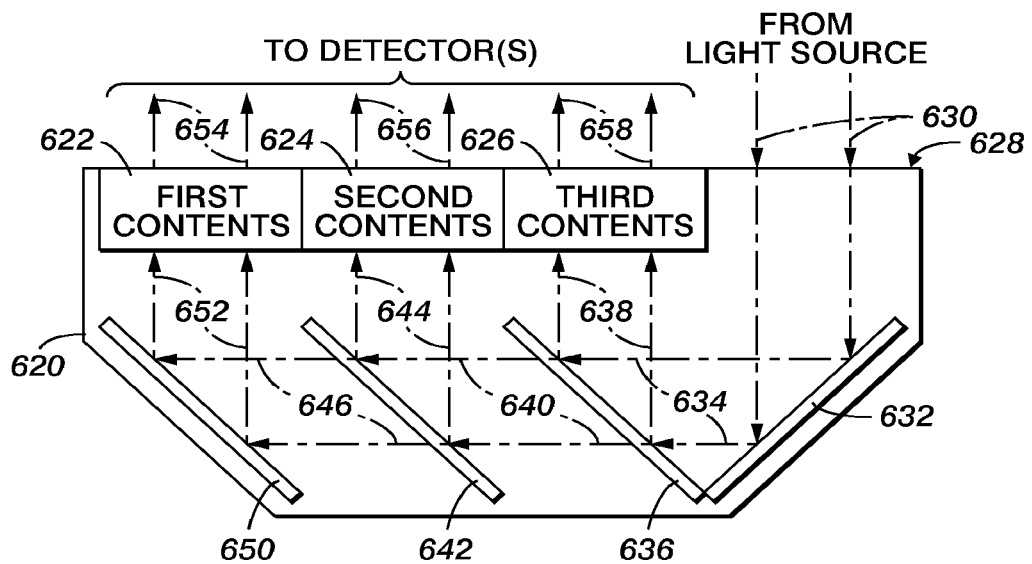
FIG. 19 is a schematic diagram of an implementation of an article that includes a reflection component.
Figure 20:
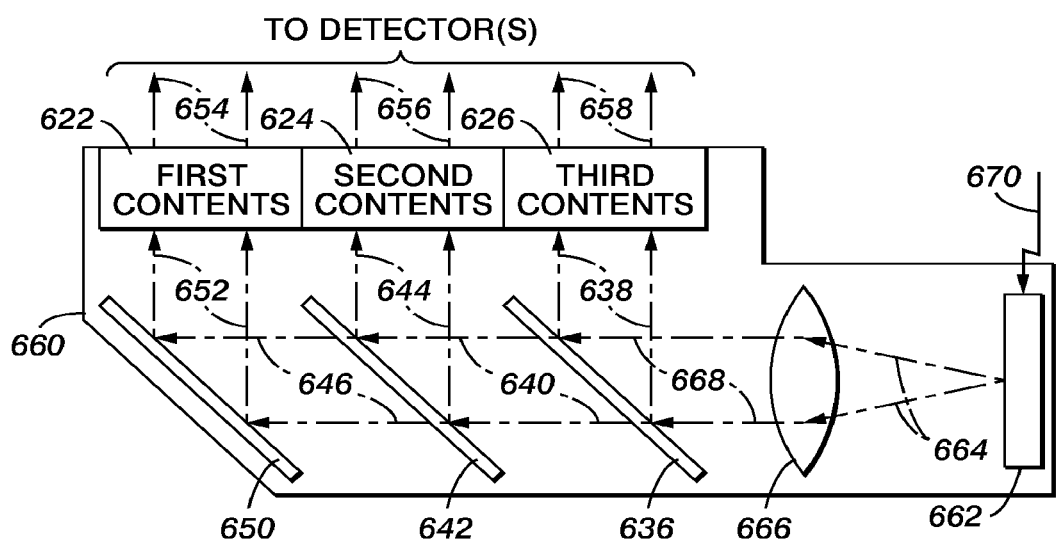
FIG. 20 is a schematic diagram of another implementation of an article with a reflection component similar to that in FIG. 19 and with a light source.
Figure 21:
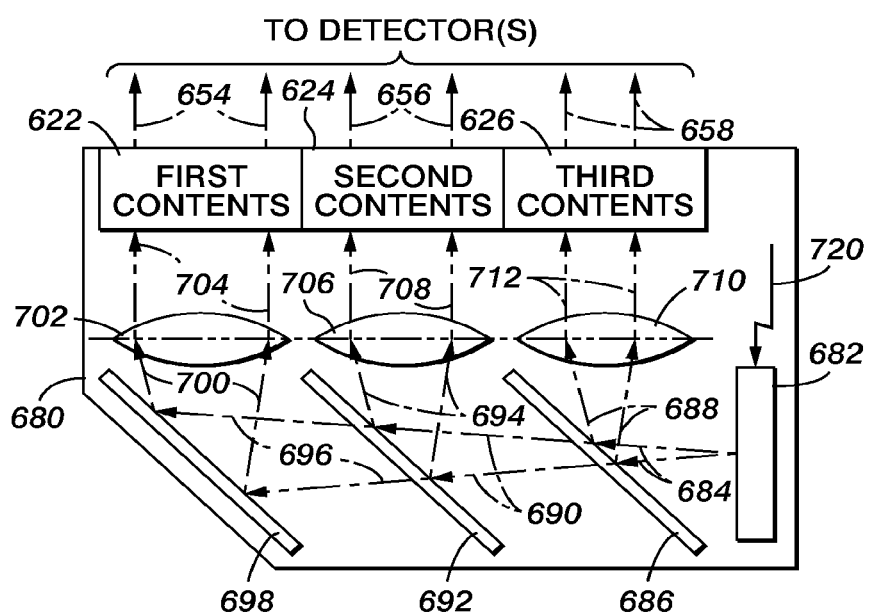
FIG. 21 is a schematic diagram of another implementation of an article with a reflection component and a light source.

FIGS. 19-21 illustrate approaches in which an implantable product with three containers includes a reflection component that divides incident light from a light source before providing it to the containers for operation as optical cavities that provide transmission mode output light. As in FIG. 15, these techniques avoid the need for light source and detector components on opposite sides of a body part. The exemplary implementation of FIG. 19 receives light from outside the body part but on the same side as detectors, while those of FIGS. 20-21 include a narrow beam light source in the product. Issues mentioned above in relation to FIGS. 11-18 are also relevant to FIGS. 19-21.

FIG. 19 illustrates a configuration in which implantable product 620, which could be a passive device, includes containers 622, 624, and 626, at least one of which is an analyte container and at least one of which is a non-analyte container. Product 620 also includes a reflection component with an incident light surface 628 through which incident light is received, represented by arrows 630.

Within the reflection component, mirror 632 receives the incident light in an incident light direction and provides input light, represented by arrows 634, in a perpendicular direction. Partially reflective mirror 636, such as with one-third reflectivity, receives the full intensity incident light and splits it, reflecting one-third intensity input light represented by arrows 638 in an entry direction to container 626, and transmitting two-thirds intensity light, represented by arrows 640. Partially reflective mirror 642, such as with one-half reflectivity, receives the two-third intensity light and splits it, reflecting one-third intensity input light represented by arrows 644 in an entry direction to container 624, and transmitting one-third intensity light, represented by arrows 646. Totally reflective mirror 650 receives the one-third intensity light and reflects it, providing one-third intensity input light represented by arrows 652 in an entry direction to container 622. In response, the optical cavities provide respective transmission mode output light, represented by arrows 654, 656, and 658 for photosensing, such as by appropriately positioned detectors that include discrete photosensors or a photosensing array.

FIG. 20 illustrates a configuration in which implantable product 660 includes parts similar to those of product 620 (FIG. 19), with counterpart parts that operate substantially the same way being labeled with the same reference numbers. In addition, product 660 includes narrow beam light source 662, such as a tunable VCSEL laser. The narrow beam from source 662, represented by arrows 664, is, however, somewhat divergent, and therefore passes through lens 666 or another appropriate optical collimating component, which provides a more collimated beam represented by arrows 668. The collimated beam is then received by mirror 636, and so forth as described above in relation to FIG. 19.

As in FIGS. 13 and 14, light source 662 can be controlled from outside a body part by control signals, represented by arrow 670. As a result, product 660 would require some sort of power source for light source 662, as in some of the exemplary implementations described above.

FIG. 21 illustrates another configuration in which implantable product 680 includes some parts similar to those of products 620 (FIG. 19) and 660 (FIG. 20), with counterpart parts that operate substantially the same way being labeled with the same reference numbers. In addition, product 660 similarly includes narrow beam light source 682, such as a tunable VCSEL laser whose output beam does not diverge as rapidly as in FIG. 20. The narrow beam from source 682, represented by arrows 684, is divided before being collimated rather than after being collimated as in FIG. 20. The collimating techniques of FIGS. 20 and 21 could in principal be used together if advantageous, and more complex optical components might be capable of combining dividing and collimating operations.

Within the reflection component in FIG. 21, partially reflective mirror 686, such as with one-third reflectivity, receives the full intensity narrow beam and splits it, reflecting a one-third intensity narrow beam represented by arrows 688 in an entry direction to container 626, and transmitting a two-thirds intensity narrow beam, represented by arrows 690. Partially reflective mirror 692, such as with one-half reflectivity, receives the two-third intensity narrow beam and splits it, reflecting a one-third intensity narrow beam represented by arrows 694 in an entry direction to container 624, and transmitting a one-third intensity narrow beam, represented by arrows 696. Totally reflective mirror 698 receives the one-third intensity narrow beam and reflects it, providing a one-third intensity narrow beam represented by arrows 700 in an entry direction to container 622.

Also within the reflection component, lens 702 or another appropriate optical collimating component collimates the narrow beam from mirror 698, providing a collimated beam represented by arrows 704 to container 622. Similarly, lenses 706 and 710 collimate the respective narrow beams from mirrors 692 and 686, providing collimated beams represented by arrows 708 and 712, respectively. In response, the optical cavities provide respective transmission mode output light as above.

As in FIG. 20, light source 682 can be controlled from outside a body part by control signals, represented by arrow 720. As a result, product 680 would also require some sort of power source for light source 682.

Implementations as in FIGS. 19-21 could also be advantageous for reasons set forth above. In addition, they provide an elegant technique to increase the number of containers that can be operated as optical cavities, which are limited for some other configurations. Assuming suitable fluidic components for analyte, non-analyte, and reference containers, various suitable arrangements could be provided, including arrangements with more than three containers, and also more than three mirrors to provide their input light.

Figure 22:
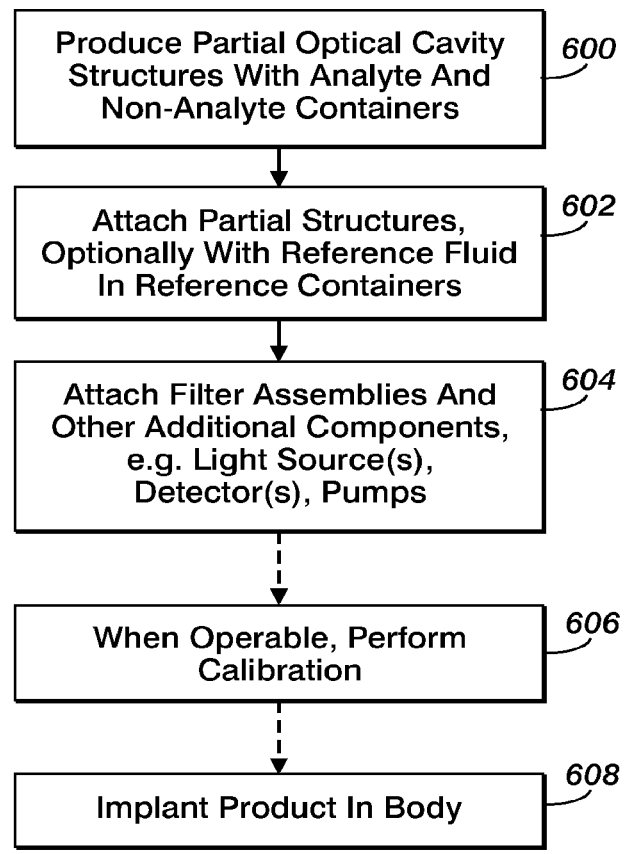
FIG. 22 is a flowchart showing operations in producing and using implantable products.

FIG. 22 illustrates exemplary operations in producing products like implantable products 360, 390, 400, 420, 440, 460, 480, 500, 520, 550, 570, 620, 660, and 680 in FIGS. 8-21. In particular, the operations in FIG. 22 make it possible to produce implantable products that include analyte and non-analyte containers, each of which is within a respective optical cavity that can be operated to provide output light in one or more modes with information about optical characteristics of analyte and non-analyte contents.

The operation in box 600 in FIG. 22 produces two partial optical cavity structures. This operation can include producing a light-reflective structure on each of two substrates, similar to light-reflective structures described above, such as in relation to FIG. 8. This operation can also include producing a patterned layer of SU-8 or polydimethylsiloxane (PDMS) on one or both of the light-reflective structures, such as with techniques described in co-pending U.S. patent application Ser. No. 11/315,992, entitled "Sensing Photons from Objects in Channels" and incorporated herein by reference in its entirety. Each patterned layer could include structures such as wall-like part 24 in FIG. 1 and wall 314 in FIG. 6, together with other wall-like structures that partially enclose analyte and non-analyte containers, and that could completely enclose additional reference containers as in FIGS. 9-10. If appropriate, an anti-adhesive coating can be applied to surfaces of the partial structures, such as by dip-coating polyethylene glycol (PEG) or by providing a coating of parylene C or vapor deposit tetraglyme; these measures may be helpful in extending the operating life of an implantable product, by preventing clogging.

The two partial structures can also have appropriate dimensions to satisfy various constraints. For example, for a compact, minimally invasive, disposable product, small dimensions are required. The volume of each of the resulting analyte and non-analyte containers, for example, could be as small as a few 100 pl; even with a very small volume, adequate light-analyte interaction can occur in an optical cavity if reflectivity of reflection surfaces is sufficiently high. At the same time, dimensions must be chosen that can produce the desired optical cavity modes over the desired range of photon energies with the available illumination, such as to obtain an absorption spectrum or to measure refractive index dispersion; for example, the number of modes depends on the distance between reflection surfaces bounding the cavity.

The operation in box 602 then attaches the two partial structures, optionally with reference fluid (liquid or gas) in each reference container, if any. Reference fluid filling could be implemented in many different ways, including, for example, filling each reference container before attaching the partial structures or, alternatively, attaching the partial structures and then inserting fluid into each reference container, such as through a needle, after which an appropriate operation could be performed to ensure the reference container is sealed. The reference fluid can be water, as mentioned above, or any other appropriate fluid with a known refractive index. Due to possible difficulties with reference fluid filling, use of an appropriate reference solid or semi-solid in each reference container might be advantageous. The operation in box 602 can also include forming a suitable bond between the two partial structures so that they are firmly attached to each other.

The operation in box 604 then attaches the filter assemblies for the analyte and non-analyte containers and any other additional components necessary to complete the product. For example, if the product is implemented as in FIG. 10, pumping devices must be attached by the operation in box 604. Similarly, if implemented as in FIG. 12 or 13, detector 436 or detector 466 must be attached by the operation in box 604. Or, if implemented as in FIG. 13 or 14, light source 468 or light source 480 must be attached to the product by the operation in box 604. Or, if implemented as in FIG. 15, reflection component 506 must be attached to the product by the operation in box 604. The operation in box 604 can also include any other internal or external electrical, optical, or fluidic connections necessary for operation of the product, such as connections to coupling circuitry as in FIG. 8, or, alternatively, such connections could later be made at the time the product is implanted.

The choice of a detector can be based on several constraints. For example, if intensities are sensed as wavelength is scanned, as mentioned above, simple discrete photosensors could be used. For broader band illumination, if intensity peaks of a small number of modes are photosensed to detect changes in central energy or position, amplitude, contrast, and FWHM, it may be possible to use a respective one-dimensional photosensing array for each optical cavity, with each array including a relatively small number of cells, reducing the electrical power requirement because less power is dissipated in the detector. In general, compactness is promoted by using a photosensing IC, as described in co-pending U.S. Pat. No. 7,471,399 and incorporated by reference herein in its entirety.

The operation in box 606 can be performed at any appropriate time after the product is operable, as suggested by the dashed line from box 604 to box 606, and may not be necessary if self-calibration as described above provides satisfactory results. The operation in box 606 performs calibration, which requires appropriate electrical and optical operations, which may require connections of circuitry. In any case, calibration in box 606 can include obtaining items of data or data structures to be used in obtaining analyte information as described herein, and the data or data structures can be stored in memory 246 as part of calibration data 276 (FIG. 5), or, in appropriate cases, can be embedded in analyte information routine 274 or stored in another appropriate form. In particular, the operation in box 606 can include operations that produce one or more calibration tables or reference curves for the reference fluid, such as under different temperatures or other environmental conditions.

Finally, the operation in box 608 implants the resulting product in a body, such as in a human body, to monitor an analyte such as glucose. If the product is sufficiently small, implantation can be performed simply by pushing the product through the skin into an appropriate part of the body in which the analyte and non-analyte containers will be filled with blood, lymph, interstitial fluid, or other bodily fluid.

In general, the operations in any of boxes 600, 602, 604, 606, and 608 can include additional activities. For example, at any appropriate point in production of the product, electrical or optical connections can be made so that signals can be provided as necessary. Similarly, connections can be made at any appropriate time to provide electrical power.

The technique of FIG. 22 could be modified in many ways within the scope of the invention. For example, the operations in boxes 600, 602, and 604 could be combined in any appropriate way to facilitate attachment of components in a desired sequence. Furthermore, the technique of FIG. 22 is extremely general, and could be employed to produce a wide variety of different products that can be implanted within a body to obtain information about analytes in bodily fluids.

The implementations described above could be applied in many ways, but an especially important area of application is in continuous or frequent monitoring of glucose concentration as is needed for diabetes management and reduction of complications. Fast, precise, and constant or even continuous glucose monitoring would help ensure detection of episodes of hyper- and hypoglycemia. Current techniques, such as finger-sticking to obtain a blood sample and use of implantable devices with electrochemical measurement, have various difficulties that might be overcome with a compact optical device.

The implementations described above are consistent with a compact, minimally invasive, disposable product that could be implanted to allow optical measurement of glucose concentration in a small volume of bodily fluid. Such a product could be designed to last an appropriate length of time before it must be replaced; durations of at least two weeks are believed to be achievable with low power consumption measures. It is also believed possible to produce such products at a sufficiently low cost to make disposable versions feasible.

In using such a product, a defined characterization volume of the bodily fluid would be positioned in each of an analyte container and a non-analyte container, each in a respective optical cavity. If a reference container is also provided in a respective optical cavity, it might also be possible to perform continuous self-calibration with a reference fluid under the same environmental conditions and enhanced sensitivity and specificity, offering the possibility of further reducing or eliminating the effect of tissue and skin perturbations on measurements.

As described above, features of intensity peaks of an optical cavity's modes can provide information about several optical characteristics of glucose, including absorption spectrum, refractive index dispersion, either or both of which can be measured at discrete sampling points of the energy spectrum. Precise information, such as about central energy, amplitude, contrast, and FWHM of an intensity peak, can be obtained for each sampling point with a chip-size detector, as described in co-pending U.S. Pat. No. 7,471,399 and incorporated by reference herein in its entirety. The information could be obtained in digital form, allowing data processing, which can obtain information with adequate sensitivity and specificity with improved signal-to-noise ratio. In addition to self-calibration using reference fluid as mentioned above, photosensed quantities and sensing results could be adjusted in various other ways, such as with contrast-based adjustment, such as by measuring a peak-to-valley ratio to obtain the finesse, which is a measure of absorption for a given Fabry-Perot etalon; other contrast-based adjustment techniques are described in co-pending U.S. Pat. No. 7,502,123 and incorporated herein by reference in its entirety.

With data processing techniques that provide sufficient sensitivity, concurrently obtaining the absorption spectrum and refractive index dispersion in the near infrared range, at wavelengths between approximately 2.1-2.5 µm, may assist in determining glucose concentration. Refractive index information contains absorption information from other spectral ranges, in accordance with the Kramers-Kronig relation, and therefore can provide additional information on glucose concentration in a multiple signal analysis. Multiple signal analysis could be extended by measuring in multiple wavelength ranges, especially in spectral bands that provide key information on glucose level. It may be possible to perform additional characterization techniques using the same implantable product, such as optical polarimetry and fluorescence. Information could also be used from electrical techniques such as conductivity or capacitance measurement.

Some of the implementations described above in relation to FIGS. 1-22 are examples of implantable articles that include first and second parts, each including a container and being operable as an optical cavity. An optical spectrum characteristic of the cavity can be affected by presence of spectrum-affecting objects in each container, and each container can have a set of bounding regions through which objects in bodily fluid can transfer between its interior and exterior when implanted in a body. The article can also include fluidic components that control transfer of objects in bodily fluids through the bounding regions: one fluidic component can permit transfer of a first set of spectrum-affecting objects into the first container at a more rapid rate than other objects, while another can permit transfer of a second set of such objects into the second container at a more rapid rate than other objects. The first and second sets can both include a shared subset, while the first set can include a non-shared subset that the second set does not include. Objects that are instances of an analyte type can predominantly in this non-shared subset.

In specific implementations, the article can also include a third part that is operable as a reference optical cavity, into which spectrum-affecting objects in bodily fluid are not transferred during operation. The third part can be between the first and second parts, each of which can have filter assemblies on a non-optical side disposed away from the other. Also, each of the first and second parts can include an unattached side, an attached side, and lateral surface between its unattached and attached sides; each part's fluidic component can include a filter assembly that permits transfer through an area equal to approximately 75% or more of the area of its lateral surface.

In further specific implementations, the fluidic components of the first and second parts can each include a large molecule filter that prevents transfer of large molecules, while the second part's filter assembly can also include a small molecule filter that permits transfer only of small molecules and/or a selective filter that permits transfer only of a selected set of molecule types. The selected filter can, for example, be an ionophore membrane.

In further specific implementations, the article can have an incident light surface to receive light in an incident direction from outside a surface region of a body, and the parts and the incident light surface can be configured so that each part can respond to the incident light by operating as an optical cavity providing output light in transmission or reflection modes, indicating information about its contents. The article can also include a reflection component, configured so that it receives transmission mode output light in the incident direction and reflects it in an exit direction toward the surface region of the body, approximately opposite the incident direction.

In further specific implementations, the article can include a light source that provides a light beam, and an optical cavity, that receives and divides the light beam into partial beams that are provided to the parts. The light source can be a laser and the optical component can collimate the light beam before dividing it and/or collimate the partial light beams before providing them to the parts. The article can also include a light exit surface for each of the parts to provide output light, and the light exit surfaces can be aligned to provide the output light in approximately an exit direction.

In further specific implementations, each of the parts can include interface surfaces at which it receives input light and/or provides output light. The interface surfaces of each part can include an entry surface and an exit surface, with the entry surfaces aligned to receive light in an entry direction and the exit surfaces aligned to provide it in an exit direction. Each part can receive input light in any of a range or set of entry directions and can provide output light in any of a range or set of exit directions; in a transmission mode, for example, each part's exit direction can be approximately the same as its entry direction, while in a reflection mode, each parts exit direction can be approximately opposite or oblique to its entry direction. Each part can provide reflection mode output light through the same interface surface through which it receives input light, and the parts' interfaces can be aligned or oblique to each other. The article can include a reflection component configured to receive incident light in an incident direction different than the entry direction of the parts and/or to receive transmission mode output light in the exit direction from the parts and provide reflected output light in a different reflected direction; the incident direction and the reflected direction can be approximately perpendicular or approximately opposite.

In further specific implementations, each part can operate as a Fabry-Perot cavity, and each can operate as a homogeneous optical cavity, such as providing output light in one or more modes. Each spectrum characteristic can be a feature with a central photon energy, and the spectrum-affecting objects can shift the central energy. Each characteristic can be a transmission mode peak or a reflection mode valley.

Some of the implementations described in relation to FIGS. 1-22 also illustrate examples of a method that controls transfer of objects in bodily fluid between interior and exterior of containers implanted in a body. Each container is in part of an implantable article that is operable as an optical cavity, and each container has a set of bounding regions through which objects in bodily fluid can transfer between its exterior and interior. The method also operates the part of each container as an optical cavity to provide output light in which a spectrum characteristic is affected by presence of spectrum-affecting objects or an optical spectrum feature is shifted by presence of spectrum-shifting objects in the container. The method can permit transfer of a first set of spectrum-affecting or spectrum-shifting objects into the first container at a more rapid rate than other objects, and permit transfer of a second set into the second container at a more rapid rate, with the sets including shared and non-shared subsets as above, with objects of an analyte type or set predominantly in the non-shared subset and with output light from the containers together including information about objects of the analyte type or set.

In specific implementations, the shared subset includes electrolytes ions and the shared subset can include predominantly molecules of a set of selected types, such as sodium chloride. The analyte can be glucose, and the method can photosense output light from the containers and use sensing results to obtain information about glucose concentration. Photosensing can be performed with a discrete detector of intensity of each container's output light. If the spectrum characteristic is shifted, the method can use the sensing results to obtain a shift value for each container and then use the shift values to obtain glucose concentrations. If the article has a third part operable as a reference optical cavity, as above, the method can obtain shift values for all three containers, using the shift values for the second and third containers to obtain an absolute measurement and then using that with the shift value for the first container to obtain glucose information. The second container's shift can indicate shift by a set of selected electrolyte types, such as sodium chloride, or the shared subset can include predominantly objects smaller than glucose.

In further specific implementations, the method can permit transfer of a third set of spectrum-affecting objects into each of the containers only at a slower rate than spectrum-affecting objects that are not in third set. A subset of the third set can be permitted to transfer only at negligible rates or zero rates. The third set can include predominantly objects larger than objects in the non-shared subset, such as objects weighing at least approximately 30 kDa.

The method can include a series of iterations, during each of which the parts are illuminated at a respective photon energy that is different for different iterations. A tunable laser can illuminate, and the method can change its energy between two consecutive iterations. Further, photosensing can be performed during each iteration to obtain an intensity value and the intensity value can be used to obtain information about the analyte.

In further specific implementations, the method can obtain optical-based data indicating information about each part's spectrum characteristics and, for at least one container, electrical-based data indicating information about electrical characteristics; the optical-based data and electrical-based data can be used to obtain information about analytes. The electrical characteristic can be conductance, and AC capacitance can be measured across a container.

Some of the implementations described above in relation to FIGS. 1-22 are examples of implantable systems that include an optical subsystem and a fluidic subsystem. The optical subsystem system can include two or more parts including first and second parts as described above. The fluidic subsystem can control transfer of objects as described above.

Some of the implementations described above in relation to FIGS. 1-22 also illustrate examples of a method of making an implantable product. The method produces an optical cavity structure that includes first and second parts, each operable as an optical cavity. In doing so, the method produces the parts to each include a container with bounding regions through which objects in bodily fluid can transfer between the container's interior and exterior when the product is implanted in a body. The method also produces each optical cavity so that, when operated as a cavity, it has a respective optical spectrum characteristic that can be affected by spectrum-affecting objects in the container. The method attaches fluidic components to the parts, and the fluidic components control transfer of objects in bodily fluid through the bounding regions when the product is implanted. The first part's fluidic component permits transfer of a first set of spectrum-affecting objects into the first container at a more rapid rate than other objects, and the second fluidic component permits transfer of a second set into the second container at a more rapid rate than other objects. The first and second sets both include a shared subset, while the first set includes a non-shared subset. Objects that are instances of an analyte are predominantly in the non-shared subset.

The implementations in FIGS. 1-22 illustrate various applications of techniques as described above, including implantable articles that include optical cavity structures with analyte, non-analyte, and, in some cases, reference containers. Fluidic components such as filter assemblies control transfer of objects in bodily fluids into analyte and non-analyte containers. The articles can be implanted in bodies and used to obtain information about an analyte such as glucose in bodily fluid, such as about its refractive index and absorption coefficient.

Techniques that use implantable products to obtain information about analytes, as exemplified by the implementations in FIGS. 1-22, can be applied in various diagnostic and monitoring applications, in which a compact, inexpensive, disposable product would be highly desirable. Information about refractive index and absorption, for example, could be used to identify presence or concentration of glucose or another analyte indicating a disease condition.

Some of the techniques described above have been successfully implemented or simulated, including the production and operation of a highly sensitive optical cavity structure that has analyte and non-analyte containers, output light from which can be photosensed to obtain information about glucose concentration.

The exemplary implementations described above allow compact, inexpensive implantable products for selectively measuring glucose or another analyte with great sensitivity. In general, the techniques can be implemented using existing photosensors and light sources.

The exemplary implementations described above employ optical cavities with specific parameters and modes, but a wide variety of cavities could be used. For example, the above exemplary implementations generally involve homogeneous cavities, but inhomogeneous cavities could be used. Cavities with widths in the range from a few microns to millimeters are feasible, and output light ranging from the ultraviolet up to the far infrared could be sampled.

Components of exemplary implementations as described above could have various shapes, dimensions, or other numerical or qualitative characteristics other than those illustrated and described above. For example, although square entry surfaces as described may be advantageous for illumination and although and sizes around 1 mm are readily manufacturable, optical cavities could have any suitable shapes and dimensions. Similarly, although the exemplary implementations generally involve two or three containers, several implementations could readily be modified to include one or more additional containers, with each additional container being for analyte, non-analyte, or reference; the containers could be arranged in a wide variety of ways, some of which are shown or described above.

Some of the above exemplary implementations involve specific types of fluidic components, light source components, and detectors, but the invention could be implemented with a wide variety of other types of components. For example, filters described above select specific types of objects or permit specific sizes of objects to transfer, but the invention might be implemented with other fluidic components that control transfer of objects in bodily fluid into containers. Also, some exemplary implementations use current controlled VCSELs for illumination across a subrange of wavelengths, but many of types of light sources could be used in appropriate numbers and arrangements, tuned in various ways, and in various wavelength ranges. Further, some exemplary implementations use discrete photosensors, but various ICs with photosensing arrays or even position-sensitive detectors (PSDs) might be used.

Some of the above exemplary implementations involve specific analytes, e.g. glucose, and specific types of other spectrum-affecting or spectrum-shifting objects, e.g. sodium chloride, found in specific bodily fluids, e.g. interstitial fluid, but these are merely exemplary. The invention could be implemented in relation to any appropriate spectrum-affecting or spectrum-shifting analytes and other objects, such as other molecules or possibly even ions or other non-molecular entities, and for any bodily fluid, whether in a human or in a non-human animal.

Some of the above exemplary implementations involve specific materials, such as in optical cavity structures and photosensing components, but the invention could be implemented with a wide variety of materials and with layered structures with various combinations of sublayers. In particular, optical cavity structures could be fabricated with any appropriate techniques, including thin film technology such as sputtering, e-beam or thermal evaporation with or without plasma assistance, epitaxial growth, MBE, MOCVD, and so forth. To produce Bragg mirrors, appropriate pairs of materials with low absorption coefficients and large difference in refractive indices could be chosen, bearing in mind the photon energies of interest; exemplary materials include $SiO_2/TiO_2$, $SiO_2/Ta_2O_5$, GaAs/AlAs, and GaAs/AlGaAs. Thicknesses of layer in optical cavity structures may vary from 30 nm up to a few hundred nanometers.

Some of the above exemplary implementations could involve particular types of optical cavity structures, such as Bragg mirrors and paired distributed Bragg reflectors separated by a Fabry-Perot cavity, but, more generally, any appropriate optical cavity structure could be used. Various techniques could be used to produce optical cavity structures in addition to those described above.

The exemplary implementation in FIGS. 5 and 7 employs a CPU, which could be a microprocessor or any other appropriate component. Furthermore, as noted above, operations on photosensed quantities, such as to obtain shift values, other effect values, differential quantities, or values indicating glucose presence or concentration, could be performed digitally or with analog signals, and could be done either on the same IC as a photosensor array, on other components, or on a combination of the two, with any appropriate combination of software or hardware.

The above exemplary implementations generally involve production and/or use of optical cavity structures, light sources, photosensors, processing circuitry, and control circuitry following particular operations, but different operations could be performed, the order of the operations could be modified, and additional operations could be added within the scope of the invention. For example, readout of adjusted or unadjusted photosensed quantities from an IC could be performed serially or in parallel, and could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. An article comprising:
   first and second parts; each of the first and second parts including a respective container and being configured to form an optical device comprising a first light reflective component having a first reflective surface that is at least partially reflective and a second light reflective component having a second reflective surface that is at least partially reflective arranged to face the first reflective surface, the optical device having a light-transmissive region that is at least partially bounded by the first and second reflective surfaces of the light-reflective components, the light-reflective components and the light-transmissive region configured to reflect light more than once across the light-transmissive region, the first light reflective component configured to allow input light to enter the light-transmissive region through the first light reflective surface; and one or both of the first light reflective component and the second light reflective component configured to allow output light to exit the light-transmissive region through the one or both of the first light reflective surface and the second light reflective surface, the optical device having a respective optical spectrum characteristic that can be affected by presence of spectrum-affecting objects in the container; the optical spectrum characteristic providing the output light in response to the input light in a set of optical modes providing higher intensity light in some photon energy subranges relative to light in other photon energy subranges, the modes spaced apart as a function of photon energy, the respective container having a respective set of one or more bounding regions through which objects in fluid can transfer between the container's interior and exterior; and
   first and second fluidic components that control transfer of objects in fluid through the respective bounding regions of the first and second parts, respectively; the first fluidic component permitting transfer of a first set of the spectrum-affecting objects into the light transmissive region of first container at a more rapid rate than spectrum-affecting objects not in the first set; the second fluidic component permitting transfer of a second set of the spectrum-affecting objects into the light transmissive region of the second container at a more rapid rate than spectrum-affecting objects not in the second set; the first and second sets of spectrum-affecting objects both including a shared subset; the first set including a non-shared subset that the second set does not include; objects that are instances of an analyte type being predominantly in the non-shared subset.

2. The article of claim 1, further comprising:
   a third part that is configured as a reference optical device with a respective optical spectrum characteristic; in operation, spectrum-affecting objects in fluid not transferring into the third part.

3. The article of claim 2 in which the third part is between the first and second parts; the first and second parts having respective first and second non-optical sides disposed away from each other; the first and second fluidic components including filter assemblies at the first and second non-optical sides, respectively.

4. The article of claim 1 in which the first and second parts include respective first and second unattached sides disposed away from each other, respective first and second attached sides disposed toward each other, and respective first and second lateral surfaces extending between the first and second unattached and attached sides, respectively; the first and second fluidic components including respective first and second filter assemblies, respectively, each permitting transfer through an area equal to approximately 75% or more of the area of the respective lateral surface.

5. The article of claim 1 in which the first and second fluidic components include first and second filter assemblies, respectively, each including a respective large molecule filter that prevents transfer of large molecules, the second filter assembly further including at least one of:
   a small molecule filter that permits transfer only of small molecules; and
   a selective filter that permits transfer only of a set of selected types of molecules.

6. The article of claim 1, further comprising:
   an incident light surface that can receive incident light in an incident direction; each of the first and second parts and the incident light surface being configured so that the part can respond to incident light in the incident direction by operating as an optical device providing respective output light in one or more of transmission and reflection modes, the output light indicating information about contents of the part's container.

7. The article of claim 6, further comprising:
   a reflection component; the first and second parts and the reflection component being configured so that the reflection component can receive transmission mode output light provided in the incident direction and reflect the transmission mode output light in an exit direction, the exit direction being approximately opposite the incident direction.

8. The article of claim 1, further comprising:
   a light source that, in operation, provides a light beam; and
   an optical component that receives and divides the light beam into partial beams and provides first and second partial beams to the first and second parts, respectively.

9. The article of claim 8 in which the light source is a laser and the optical component further performs at least one of:
   collimating the light beam from the light source before dividing the light beam into partial light beams; and
   collimating the first and second partial beams before providing the first and second partial beams to the first and second parts.

10. The article of claim 1 in which each of the first and second parts further includes:
    one or more respective interface surfaces at which the first and second parts can receive input light and/or provide output light when operating as an optical device; each of the first and second parts, when operating as an optical device, can receive input light through one of the first and second part's interface surfaces in any of a set of respective entry directions and provide output light through one of the first and second part's interface surfaces in any of a set of respective exit directions; in operation as an optical device in response to input light at one of the first and second part's set of entry directions, each part's exit direction being one of:
        approximately the same as the entry direction;
        approximately opposite to the entry direction; and
        oblique to the entry direction.

11. The article of claim 10 in which, in response to input light in the entry direction, each part's exit direction is approximately opposite or oblique to the entry direction; each of the first and second parts providing reflection mode output light, receiving input light and providing output light through the same one of each of the first and second part's interface surfaces.

12. The article of claim 11 in which the first and second parts have interface surfaces that are one of:
   aligned with each other;
   oblique to each other.

13. The article of claim 10 in which each of the first and second parts provides transmission mode output light; the article further comprising:
   a reflection component; the first and second parts and the reflection component being configured so that at least one of:
      the reflection component receives incident light received in an incident direction and, in response, provides input light in the entry direction, the incident direction being different than the entry direction; and
      the reflection component receives transmission mode output light provided by the first and second parts in the exit direction and, in response, provides reflected output light in an reflected direction different than the exit direction.

14. A method comprising:
   controlling transfer of objects in fluid between interior and exterior of at least two of a set of containers; each container being in a respective part of an article, the respective part being configured to form an optical device comprising a first light reflective component having a first reflective surface that is at least partially reflective and a second light reflective component having a second reflective surface that is at least partially reflective arranged to face the first reflective surface, the optical device having a light-transmissive region that is at least partially bounded by the first and second light reflective surfaces of the first and second light-reflective components, the light-reflective components and the light-transmissive region configured to reflect light within the light-transmissive region more than once across the light-transmissive region, the first light reflective component configured to allow input light to enter the light-transmissive region through the first light reflective surface; and one or both of the first light reflective component and the second light reflective component configured to allow output light to exit the light-transmissive region through the one or both of the first light reflective surface and the second light reflective surface, each of first and second containers in the set having a respective set of one or more bounding regions through which objects in fluid can transfer between the container's exterior and interior; and
   operating the respective part of each of at least the first and second containers as an optical device having a respective output spectrum characteristic that is affected by presence of spectrum-affecting objects in the container, the output spectrum characteristic providing light in a set of modes providing higher intensity light in some photon energy subranges relative to light in other photon energy subranges, the modes spaced apart as a function of photon energy;
   the act of controlling transfer of objects in fluid comprising:
      permitting transfer of a first set of the spectrum-affecting objects into the first container through the respective set of bounding regions at a more rapid rate than spectrum-affecting objects that are not in the first set; and
      permitting transfer of a second set of the spectrum-affecting objects into the second container through the respective set of bounding regions at a more rapid rate than spectrum-affecting objects that are not in the second set;
   the first and second sets of spectrum-affecting objects both including a shared subset; the first set including a non-shared subset that the second set does not include; objects that are instances of an analyte type being predominantly in the non-shared subset; output light from the first and second containers together including information about spectrum-affecting objects of the analyte type.

15. The method of claim 14 in which the shared subset includes predominantly molecules of a set of selected types.

16. The method of claim 15 in which the set of selected types includes sodium chloride molecules.

17. The method of claim 14 in which the analyte type is glucose molecules; the method further comprising:
   photosensing output light from respective parts of the first and second containers and using sensing results to obtain information about glucose concentration in the fluid.

18. The method of claim 17 in which the article further includes a third part configured as a reference optical device with a respective spectrum characteristic; in each of the parts, the respective spectrum characteristic being shifted by spectrum-affecting objects; the act of photosensing output light from the first and second parts and using sensing result comprising:
   obtaining first, second, and third shift values for the first, second, and third containers, respectively;
   using the second and third shift values to obtain an absolute measurement; and
   using the absolute measurement and the first shift value to obtain the information about glucose concentration.

19. The method of claim 14 in which act of operating the respective part of each of at least the first and second containers as an optical device comprises a series of iterations, each iteration including:
   illuminating the respective parts of the first and second containers at a respective photon energy for the iteration; the respective photon energies of at least two of the iterations being different from each other.

20. The method of claim 19 in which the act of illuminating is performed with a tunable laser,
   the tunable laser's photon energy changing between a preceding iteration and a following iteration.

21. The article of claim 1, wherein the optical device is a Fabry-Perot optical cavity.

* * * * *